(12) United States Patent
Kudis et al.

(10) Patent No.: US 6,599,860 B1
(45) Date of Patent: Jul. 29, 2003

(54) HERBICIDAL HALOGENALKYL-SUBSTITUTED 3-(4,5-DIHYDROISOXAZOL-3-YL)-BENZOYL-CYCLOHEXENONES

(75) Inventors: Steffen Kudis, Mannheim (DE); Ernst Baumann, Dudenhofen (DE); Wolfgang von Deyn, Neustadt (DE); Klaus Langemann, Worms (DE); Guido Mayer, Neustadt (DE); Ulf Misslitz, Neustadt (DE); Ulf Neidlein, Mannheim (DE); Matthias Witschel, Bad Dürkheim (DE); Karl-Otto Westphalen, Speyer (DE); Helmut Walter, Obrigheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/130,308

(22) PCT Filed: Nov. 27, 2000

(86) PCT No.: PCT/EP00/11818

§ 371 (c)(1),
(2), (4) Date: May 16, 2002

(87) PCT Pub. No.: WO01/40199

PCT Pub. Date: Jun. 7, 2001

(30) Foreign Application Priority Data

Dec. 2, 1999 (DE) .......................... 199 58 034

(51) Int. Cl.⁷ .................. A01N 43/80; C07D 261/04
(52) U.S. Cl. ........................ 504/271; 548/240
(58) Field of Search ...................... 548/240; 504/271

(56) References Cited

U.S. PATENT DOCUMENTS 6,004,903 A   12/1999   von Deyn et al.

FOREIGN PATENT DOCUMENTS

WO   96/26200   8/1996

*Primary Examiner*—Robert W. Ramsuer
(74) *Attorney, Agent, or Firm*—Keil & Weinkauf

(57) ABSTRACT

Herbicidally active haloalkyl-substituted 3-(4,5-dihydroisoxazol-3-yl)benzoylcyclohexenones of the formula I

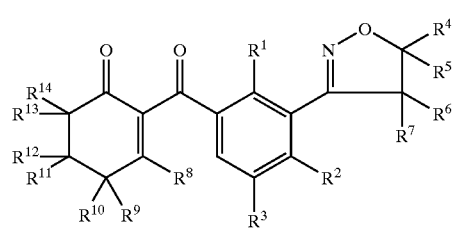

in which $R^1$ to $R^3$ and $R^5$ to $R^{14}$ are as defined in the description and $R^4$ is $C_1$–$C_4$-haloalkyl are described.

12 Claims, No Drawings

HERBICIDAL HALOGENALKYL-SUBSTITUTED 3-(4,5-DIHYDROISOXAZOL-3-YL)-BENZOYL-CYCLOHEXENONES

The present invention relates to haloalkyl-substituted 3-(4,5-dihydroisoxazol-3-yl)benzoylcyclohexenones and to processes for their preparation, to compositions comprising them and to the use of these derivatives or compositions for controlling harmful plants.

WO 96/26200 discloses herbicidal 2-benzoylcyclohexane-1,3-diones.

However, the herbicidal properties of the prior-art compounds and their compatibility with crop plants are not entirely satisfactory.

It is an object of the present invention to provide novel, in particular herbicidally active, compounds having improved properties.

We have found that this object is achieved by the haloalkyl-substituted 3-(4,5-dihydroisoxazol-3-yl) benzoylcyclohexenones of the formula I

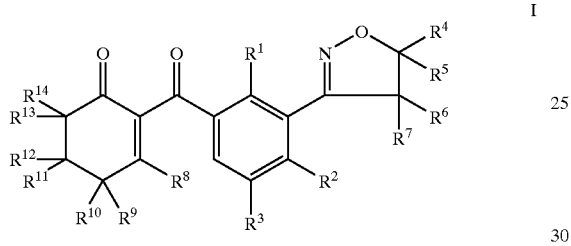

in which
$R^1$ is $C_1$–$C_6$-alkyl, $C_1$–$C_6$-haloalkyl, $C_1$–$C_6$-alkoxy or $C_1$–$C_6$-haloalkoxy;
$R^2$ is $C_1$–$C_6$-alkyl, $C_1$–$C_6$-haloalkyl, $C_1$–$C_6$-alkoxy, $C_1$–$C_6$-haloalkoxy, $C_1$–$C_6$-alkylthio, $C_1$–$C_6$-haloalkylthio, $C_1$–$C_6$-alkylsulfinyl, $C_1$–$C_6$-haloalkylsulfinyl, $C_1$–$C_6$-alkylsulfonyl, $C_1$–$C_6$-haloalkylsulfonyl, halogen, cyano or nitro;
$R^3$ is hydrogen, $C_1$–$C_6$-alkyl or halogen;
$R^4$ is $C_1$–$C_4$-haloalkyl;
$R^5$, $R^6$, $R^7$ independently of one another are hydrogen, $C_1$–$C_4$-alkyl or $C_1$–$C_4$-haloalkyl;
$R^8$ is hydroxyl, mercapto, halogen, $OR^{15}$, $SR^{15}$, $SOR^{16}$ or $SO_2R^{16}$;
$R^9$, $R^{13}$ independently of one another are hydrogen, $C_1$–$C_4$-alkyl, $C_1$–$C_4$-alkylthio or $C_1$–$C_4$-alkoxycarbonyl;
$R^{10}$, $R^{12}$, $R^{14}$ independently of one another are hydrogen or $C_1$–$C_4$-alkyl;
$R^{11}$ is hydrogen, hydroxyl, halogen, $C_1$–$C_6$-alkyl, $C_1$–$C_6$-haloalkyl, di(Ci-$C_6$-alkoxy)methyl, ($C_1$–$C_6$-alkoxy)($C_1$–$C_6$-alkylthio)methyl, di($C_1$–$C_6$-alkylthio)methyl, $C_1$–$C_6$-alkoxy, $C_1$–$C_6$-haloalkoxy, $C_1$–$C_6$-alkylthio, $C_1$–$C_6$-haloalkylthio, $C_1$–$C_6$-alkoxycarbonyl, $C_1$–$C_6$-haloalkoxycarbonyl, 1,3-dioxolan-2-yl, 1,3-dioxan-2-yl, 1,3-oxathiolan-2-yl, 1,3-oxathian-2-yl, 1,3-dithiolan-2-yl or 1,3-dithian-2-yl, where the six lastmentioned radicals may carry one, two or three substituents selected from $C_1$–$C_4$-alkyl; or
$R^9$ and $R^{10}$ or $R^{13}$ and $R^{14}$ together are $C_1$–$C_5$-alkanediyl which may carry one, two or three substituents selected from the group consisting of halogen, cyano, $C_1$–$C_4$-alkyl, $C_1$–$C_4$-haloalkyl and $C_1$–$C_4$-alkoxycarbonyl; or
$R^{10}$ and $R^{11}$ or $R^{13}$ and $R^{14}$ together are a chemical bond or $C_1$–$C_5$-alkanediyl which may carry one, two or three substituents selected from the group consisting of halogen, cyano, $C_1$–$C_4$-alkyl, $C_1$–$C_4$-haloalkyl and $C_1$–$C_4$-alkoxycarbonyl; or
$R^{10}$ and $R^{14}$ together are $C_1$–$C_4$-alkanediyl which may carry one, two or three substituents selected from the group consisting of halogen, cyano, $C_1$–$C_4$-alkyl, $C_1$–$C_4$-alkoxycarbonyl; or
$R^{11}$ and $R^{12}$ together are —O—($CH_2$)$_p$—O—, —O—($CH_2$)$_p$—S—, —S—($CH_2$)$_p$—S—, —O—($CH_2$)$_q$— or —S—($CH_2$)$_q$— which may carry one, two or three substituents selected from the group consisting of halogen, cyano, $C_1$–$C_4$-alkyl, $C_1$–$C_4$-haloalkyl and $C_1$–$C_4$-alkoxycarbonyl; or
$R^{11}$ and $R^{12}$ together are an oxygen atom;
$R^{15}$ is $C_1$–$C_6$-alkyl, $C_3$–$C_6$-alkenyl, $C_3$–$C_6$-haloalkenyl, $C_3$–$C_6$-alkynyl, $C_3$–$C_6$-cycloalkyl, $C_1$–$C_{20}$-alkylcarbonyl, $C_2$–$C_{20}$-alkenylcarbonyl, $C_2$–$C_6$-alkynylcarbonyl, $C_1$–$C_6$-alkoxycarbonyl, $C_3$–$C_6$-alkenyloxycarbonyl, $C_3$–$C_6$-alkynyloxycarbonyl, $C_1$–$C_6$-alkylthiocarbonyl, $C_1$–$C_6$-alkylaminocarbonyl, $C_3$–$C_6$-alkenylaminocarbonyl, $C_3$–$C_6$-alkynylaminocarbonyl, N,N-di($C_1$–$C_6$-alkyl)aminocarbonyl, N-($C_3$–$C_6$-alkenyl)-N-($C_1$–$C_6$-alkyl)aminocarbonyl, N-($C_3$–$C_6$-alkynyl)-N-($C_1$–$C_6$-alkyl)aminocarbonyl, N-($C_1$–$C_6$-alkoxy)-N-($C_1$–$C_6$-alkyl)aminocarbonyl, N,N-di($C_1$–$C_6$-alkyl)aminothiocarbonyl, $C_1$–$C_6$-alkoxyimino-$C_1$–$C_6$-alkyl, where the alkyl, alkoxy and cycloalkyl radicals mentioned may be partially or fully halogenated and/or may carry one, two or three substituents selected from the group consisting of cyano, $C_1$–$C_4$-alkoxy, $C_1$–$C_4$-alkylthio, di($C_1$–$C_4$-alkyl)amino, $C_1$–$C_4$-alkylcarbonyl, $C_1$–$C_4$-alkoxycarbonyl, $C_1$–$C_4$-alkoxy-$C_1$–$C_4$-alkoxycarbonyl, $C_1$–$C_4$-alkylaminocarbonyl, N,N-di($C_1$–$C_4$-alkyl)aminocarbonyl and $C_3$–$C_6$-cycloalkyl; is phenyl, phenyl-$C_1$–$C_6$-alkyl, phenylcarbonyl-$C_1$–$C_6$-alkyl, phenylcarbonyl, phenoxycarbonyl, phenoxythiocarbonyl, heterocyclyl, heterocyclyl-$C_1$–$C_6$-alkyl, heterocyclylcarbonyl-$C_1$–$C_6$-alkyl, heterocyclylcarbonyl, heterocyclyloxycarbonyl, heterocyclyloxythiocarbonyl, where the phenyl or heterocyclyl radical of the radicals mentioned may be partially or fully halogenated and/or may carry one, two or three substituents selected from the group consisting of nitro, cyano, $C_1$–$C_4$-alkyl, $C_1$–$C_4$-haloalkyl, $C_1$–$C_4$-alkoxy and $C_1$–$C_4$-haloalkoxy;
$R^{16}$ is $C_1$–$C_6$-alkyl, $C_3$–$C_6$-alkenyl, $C_3$–$C_6$-haloalkenyl, $C_3$–$C_6$-alkynyl or $C_3$–$C_6$-cycloalkyl, where the alkyl and cycloalkyl radicals mentioned may be partially or fully halogenated and/or may carry one, two or three substituents selected from the group consisting of cyano, $C_1$–$C_4$-alkoxy, $C_1$–$C_4$-alkylthio, di($C_1$–$C_4$-alkyl)amino, $C_1$–$C_4$-alkylcarbonyl, $C_1$–$C_4$-alkoxycarbonyl, $C_1$–$C_4$-alkoxy-$C_1$–$C_4$-alkoxycarbonyl, $C_1$–$C_4$-alkylaminocarbonyl, N,N-di($C_1$–$C_4$-alkyl)aminocarbonyl and $C_3$–$C_6$-cycloalkyl; is phenyl, phenyl-$C_1$–$C_6$-alkyl, phenylcarbonyl-$C_1$–$C_6$-alkyl, heterocyclyl, heterocyclyl-$C_1$–$C_6$-alkyl or heterocyclylcarbonyl-$C_1$–$C_6$-alkyl, where the phenyl or heterocyclyl radical of the radicals mentioned may be partially or fully halogenated and/or may carry one, two or three substituents selected from the group consisting of nitro, cyano, $C_1$–$C_4$-alkyl, $C_1$–$C_4$-haloalkyl, $C_1$–$C_4$-alkoxy and $C_1$–$C_4$-haloalkoxy;
p is 2, 3 or 4;

q is 1, 2, 3, 4 or 5;

and their agriculturally useful salts.

Furthermore, we have found herbicidal compositions which comprise the compounds I and have very good herbicidal activity. Moreover, we have found processes for preparing these compositions and methods for controlling undesirable vegetation using the compounds I.

Depending on the substitution pattern, the compounds of the formula I may contain one or more centers of chirality, in which case they are present as enantiomers or diastereomer mixtures. The invention provides both the pure enantiomers or diastereomers and their mixtures. The compounds of the formula I where $R^8$=OH or SH can also be present as tautomers of the structure shown, or as tautomer mixtures.

All hydrocarbon chains, i.e. alkyl, haloalkyl, dialkoxymethyl, alkoxyalkylthiomethyl, dialkylthiomethyl, alkoxy, haloalkoxy, alkylthio, haloalkylthio, alkylsulfinyl, haloalkylsulfinyl, alkylsulfonyl, haloalkylsulfonyl, dialkylamino, alkylcarbonyl, alkoxycarbonyl, haloalkoxycarbonyl, alkylthiocarbonyl, alkoxyalkoxycarbonyl, alkylaminocarbonyl, dialkylaminocarbonyl, dialkylaminothiocarbonyl, alkoxyiminoalkyl, N-alkoxy-N-alkylaminocarbonyl, phenylalkyl, heterocyclylalkyl, phenylcarbonylalkyl, heterocyclylcarbonylalkyl, alkenylcarbonyl, alkenyloxycarbonyl, alkenylaminocarbonyl, N-alkenyl-N-alkylaminocarbonyl, alkynylcarbonyl, alkynyloxycarbonyl, alkynylaminocarbonyl, N-alkynyl-N-alkylaminocarbonyl, alkenyl, alkynyl, haloalkenyl moieties can be straight-chain

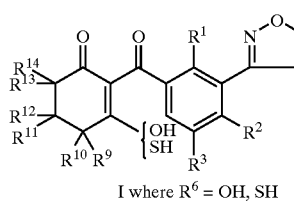

I where $R^6$ = OH, SH

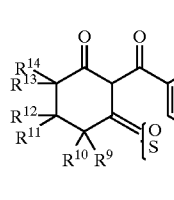

I′

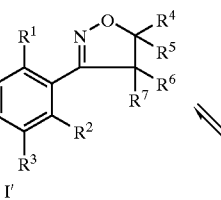

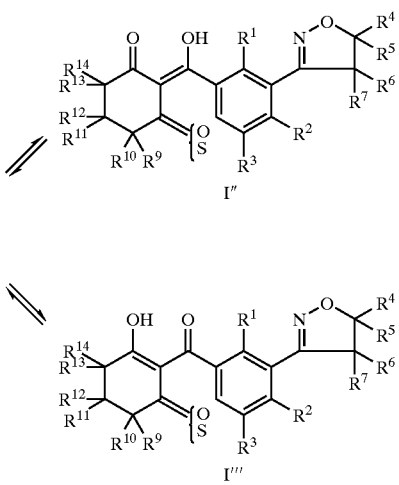

or branched. Unless indicated otherwise, halogenated substituents preferably carry one to five identical or different halogen atoms. The term halogen denotes in each case fluorine, chlorine, bromine or iodine.

Examples of other meanings are:

$C_1$–$C_4$-alkyl, and the alkyl moieties of $C_1$–$C_4$-alkylcarbonyl, phenyl-$C_1$–$C_4$-alkyl, phenylcarbonyl-$C_1$–$C_4$-alkyl, heterocyclyl-$C_1$–$C_4$-alkyl and heterocyclylcarbonyl-$C_1$–$C_4$-alkyl: for example methyl, ethyl, propyl, 1-methylethyl, butyl, 1-methylpropyl, 2-methylpropyl and 1,1-dimethylethyl;

$C_1$–$C_6$-alkyl, and the alkyl moieties of $C_1$–$C_6$-alkylcarbonyl, N-$C_3$–$C_6$-alkenyl-N-$C_1$–$C_6$-alkylaminocarbonyl, N-$C_3$–$C_6$-alkynyl-N-alkylaminocarbonyl, N-$C_1$–$C_6$-alkoxy-N-$C_1$–$C_6$-alkylaminocarbonyl, phenyl-$C_1$–$C_6$-alkyl, phenylcarbonyl-$C_1$–$C_6$-alkyl, heterocyclyl-$C_1$–$C_6$-alkyl, heterocyclylcarbonyl-$C_1$–$C_6$-alkyl and $C_1$–$C_6$-alkoxyimino-$C_1$–$C_6$-alkyl: $C_1$–$C_4$-alkyl as mentioned above, and also, for example, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1-ethyl-1-methylpropyl and 1-ethyl-3-methylpropyl;

$C_1$–$C_{20}$-alkyl as alkyl moiety of $C_1$–$C_{20}$-alkylcarbonyl: $C_1$–$C_6$-alkyl as mentioned above, and also heptyl, octyl, pentadecyl or heptadecyl;

$C_1$–$C_2$-haloalkyl: a methyl or ethyl radical as mentioned above which is partially or fully substituted by fluorine, The compounds of the formula I may also be present in the form of their agriculturally useful salts, the nature of the salt generally being immaterial. In general, the salts of those cations and the acid addition salts of those acids are suitable whose cations and anions, respectively, do not adversely affect the herbicidal action of compounds I.

Suitable cations are, in particular, ions of the alkali metals, preferably lithium, sodium and potassium, the alkaline earth metals, preferably calcium and magnesium, and the transition metals, preferably manganese, copper, zinc and iron, and also ammonium where, if desired, one to four hydrogens may be replaced by $C_1$–$C_4$-alkyl, hydroxy-$C_1$–$C_4$-alkyl, $C_1$–$C_4$-alkoxy-$C_1$–$C_4$-alkyl, hydroxy-$C_1$–$C_4$-alkoxy-$C_1$–$C_4$-alkyl, phenyl or benzyl, preferably ammonium, dimethylammonium, diisopropylammonium, tetramethylammonium, tetrabutylammonium, 2-(2-hydroxyeth-1-oxy)eth-1-ylammonium, di(2-hydroxyeth-1-yl)ammonium, trimethylbenzylammonium, furthermore phosphonium ions, sulfonium ions, preferably tri($C_1$–$C_4$-alkyl)sulfonium, and sulfoxonium ions, preferably tri ($C_1$–$C_4$-alkyl)sulfoxonium.

Anions of useful acid addition salts are primarily chloride, bromide, fluoride, hydrogen sulfate, sulfate, dihydrogen phosphate, hydrogen phosphate, nitrate, hydrogen carbonate, carbonate, hexafluorosilicate, hexafluorophosphate, benzoate and the anions of $C_1$–$C_4$-alkanoic acids, preferably formate, acetate, propionate and butyrate.

The organic moieties mentioned for the substituents $R^1$–$R^{16}$ or as radicals on phenyl rings are collective terms for individual enumerations of the individual group members.

chlorine, bromine and/or iodine, i.e., for example, chloromethyl, bromomethyl, iodomethyl, dichloromethyl, trichloromethyl, fluoromethyl, difluoromethyl, trifluoromethyl, chlorofluoromethyl, dichlorofluoromethyl, chlorodifluoromethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl or pentafluoroethyl;

$C_1$–$C_4$-haloalkyl: $C_1$–$C_2$-haloalkyl as mentioned above, and also, for example, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl and nonafluorobutyl;

$C_1$–$C_6$-haloalkyl: $C_1$–$C_4$-haloalkyl as mentioned above, and also, for example, 5-fluoropentyl, 5-chloropentyl, 5-bromopentyl, 5-iodopentyl, undecafluoropentyl, 6-fluorohexyl, 6-chlorohexyl, 6-bromohexyl, 6-iodohexyl or dodecafluorohexyl;

$C_1$–$C_4$-alkoxy and the alkoxy moieties of $C_1$–$C_4$-alkoxycarbonyl and $C_1$–$C_4$-alkoxy-$C_1$–$C_4$-alkoxycarbonyl: for example methoxy, ethoxy, propoxy, 1-methylethoxy, butoxy, 1-methylpropoxy, 2-methylpropoxy and 1,1-dimethylethoxy;

$C_1$–$C_6$-alkoxy, and the alkoxy moieties of $C_1$–$C_6$-alkoxycarbonyl, di($C_1$–$C_6$-alkoxy)methyl, ($C_1$–$C_6$-alkoxy)($C_1$–$C_6$-alkylthio)methyl, N-($C_1$–$C_6$-alkoxy)-N-($C_1$–$C_6$-alkyl)aminocarbonyl and $C_1$–$C_6$-alkoxyimino-$C_1$–$C_6$-alkyl: $C_1$–$C_4$-alkoxy as mentioned above, and also, for example, pentoxy, 1-methylbutoxy, 2-methylbutoxy, 3-methoxybutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy;

$C_1$–$C_4$-haloalkoxy: a $C_1$–$C_4$-alkoxy radical as mentioned above which is partially or fully substituted by fluorine, chlorine, bromine and/or iodine, i.e., for example, fluoromethoxy, difluoromethoxy, trifluoromethoxy, chlorodifluoromethoxy, bromodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy, 2-fluoropropoxy, 3-fluoropropoxy, 2-chloropropoxy, 3-chloropropoxy, 2-bromopropoxy, 3-bromopropoxy, 2,2-difluoropropoxy, 2,3-difluoropropoxy, 2,3-dichloropropoxy, 3,3,3-trifluoropropoxy, 3,3,3-trichloropropoxy, 2,2,3,3,3-pentafluoropropoxy, heptafluoropropoxy, 1-(fluoromethyl)-2-fluoroethoxy, 1-(chloromethyl)-2-chloroethoxy, 1-(bromomethyl)-2-bromoethoxy, 4-fluorobutoxy, 4-chlorobutoxy, 4-bromobutoxy and nonafluorobutoxy;

$C_1$–$C_6$-haloalkoxy, and the haloalkoxy moieties of $C_1$–$C_6$-haloalkoxycarbonyl: $C_1$–$C_4$-haloalkoxy as mentioned above, and also, for example, 5-fluoropentoxy, 5-chloropentoxy, 5-bromopentoxy, 5-iodopentoxy, undecafluoropentoxy, 6-fluorohexoxy, 6-chlorohexoxy, 6-bromohexoxy, 6-iodohexoxy or dodecafluorohexoxy;

$C_1$–$C_4$-alkylthio: for example methylthio, ethylthio, propylthio, 1-methylethylthio, butylthio, 1-methylpropylthio, 2-methylpropylthio and 1,1-dimethylethylthio;

$C_1$–$C_6$-alkylthio, and the alkylthio moieties of ($C_1$–$C_6$-alkoxy)($C_1$–$C_6$-alkylthio)methyl, di($C_1$–$C_6$-alkylthio)methyl and ($C_1$–$C_6$-alkylthio)carbonyl:

$C_1$–$C_4$-alkylthio, as mentioned above, and also, for example, pentylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio or 1-ethyl-2-methylpropylthio;

$C_1$–$C_4$-haloalkylthio: a $C_1$–$C_4$-alkylthio radical as mentioned above which is partially or fully substituted by fluorine, chlorine, bromine and/or iodine, i.e., for example, fluoromethylthio, difluoromethylthio, trifluoromethylthio, chlorodifluoromethylthio, bromodifluoromethylthio, 2-fluoroethylthio, 2-chloroethylthio, 2-bromoethylthio, 2-iodoethylthio, 2,2-difluoroethylthio, 2,2,2-trifluoroethylthio, 2,2,2-trichloroethylthio, 2-chloro-2-fluoroethylthio, 2-chloro-2,2-difluoroethylthio, 2,2-dichloro-2-fluoroethylthio, pentafluoroethylthio, 2-fluoropropylthio, 3-fluoropropylthio, 2-chloropropylthio, 3-chloropropylthio, 2-bromopropylthio, 3-bromopropylthio, 2,2-difluoropropylthio, 2,3-difluoropropylthio, 2,3-dichloropropylthio, 3,3,3-trifluoropropylthio, 3,3,3-trichloropropylthio, 2,2,3,3,3-pentafluoropropylthio, heptafluoropropylthio, 1-(fluoromethyl)-2-fluoroethylthio, 1-(chloromethyl)-2-chloroethylthio, 1-(bromomethyl)-2-bromoethylthio, 4-fluorobutylthio, 4-chlorobutylthio, 4-bromobutylthio and nonafluorobutylthio;

$C_1$–$C_6$-haloalkylthio: $C_1$–$C_4$-haloalkylthio as mentioned above, and also, for example, 5-fluoropentylthio, 5-chloropentylthio, 5-bromopentylthio, 5-iodopentylthio, undecafluoropentylthio, 6-fluorohexylthio, 6-chlorohexylthio, 6-bromohexylthio, 6-iodohexylthio or dodecafluorohexylthio;

$C_1$–$C_6$-alkylsulfinyl ($C_1$–$C_6$-alkyl-S(=O)—): for example methylsulfinyl, ethylsulfinyl, propylsulfinyl, 1-methylethylsulfinyl, butylsulfinyl, 1-methylpropylsulfinyl, 2-methylpropylsulfinyl, 1,1-dimethylethylsulfinyl, pentylsulfinyl, 1-methylbutylsulfinyl, 2-methylbutylsulfinyl, 3-methylbutylsulfinyl, 2,2-dimethylpropylsulfinyl, 1-ethylpropylsulfinyl, 1,1-dimethylpropylsulfinyl, 1,2-dimethylpropylsulfinyl, hexylsulfinyl, 1-methylpentylsulfinyl, 2-methylpentylsulfinyl, 3-methylpentylsulfinyl, 4-methylpentylsulfinyl, 1,1-dimethylbutylsulfinyl, 1,2-dimethylbutylsulfinyl, 1,3-dimethylbutylsulfinyl, 2,2-dimethylbutylsulfinyl, 2,3-dimethylbutylsulfinyl, 3,3-dimethylbutylsulfinyl, 1-ethylbutylsulfinyl, 2-ethylbutylsulfinyl, 1,1,2-trimethylpropylsulfinyl, 1,2,2-trimethylpropylsulfinyl, 1-ethyl-1-methylpropylsulfinyl or 1-ethyl-2-methylpropylsulfinyl;

$C_1$–$C_6$-haloalkylsulfinyl: $C_1$–$C_6$-alkylsulfinyl as mentioned above which is partially or fully substituted by fluorine, chlorine, bromine and/or iodine, i.e., for example, fluoromethylsulfinyl, difluoromethylsulfinyl, trifluoromethylsulfinyl, chlorodifluoromethylsulfinyl, bromodifluoromethylsulfinyl, 2-fluoroethylsulfinyl, 2-chloroethylsulfinyl, 2-bromoethylsulfinyl, 2-iodoethylsulfinyl, 2,2-difluoroethylsulfinyl, 2,2,2-trifluoroethylsulfinyl, 2,2,2-trichloroethylsulfinyl, 2-chloro-2-fluoroethylsulfinyl, 2-chloro-2,2-difluoroethylsulfinyl, 2,2-dichloro-2-fluoroethylsulfinyl, pentafluoroethylsulfinyl, 2-fluoropropylsulfinyl, 3-fluropropylsulfinyl, 2-chloropropylsulfinyl, 3-chloropropylsulfinyl, 2-bromopropylsulfinyl, 3-bromopropylsulfinyl, 2,2-difluoropropylsulfinyl, 2,3-difluoropropylsulfinyl, 2,3-dichloropropylsulfinyl, 3,3,3-trifluoropropylsulfinyl, 3,3,3-trichloropropylsulfinyl, 2,2,3,3,3-pentafluoropropylsulfinyl, heptafluoropropylsulfinyl, 1-(fluoromethyl)-2-fluoroethylsulfinyl, 1-(chloromethyl)-2-chloroethylsulfinyl, 1-(bromomethyl)-2-bromoethylsulfinyl, 4-fluorobutylsulfinyl, 4-chlorobutylsulfinyl, 4-bromobutylsulfinyl, nonafluorobutylsulfinyl, 5-fluoropentylsulfinyl, 5-chloropentylsulfinyl, 5-bromopentylsulfinyl, 5-iodopentylsulfinyl, undecafluoropentylsulfinyl, 6-fluorohexylsulfinyl, 6-chlorohexylsulfinyl, 6-bromohexylsulfinyl, 6-iodohexylsulfinyl or dodecafluorohexylsulfinyl;

$C_1$–$C_4$-alkylsulfonyl ($C_1$–$C_4$-alkyl-S(=O)$_2$—), and the alkylsulfonyl moieties of $C_1$–$C_4$-alkylsulfonyloxy: for example methylsulfonyl, ethylsulfonyl, propylsulfonyl, 1-methylethylsulfonyl, butylsulfonyl, 1-methylpropylsulfonyl, 2-methylpropylsulfonyl and 1,1-Dimethylethylsulfonyl;

$C_1$–$C_6$-alkylsulfonyl: a $C_1$–$C_4$-alkylsulfonyl radical as mentioned above, and also, for example, pentylsulfonyl, 1-methylbutylsulfonyl, 2-methylbutylsulfonyl, 3-methylbutylsulfonyl, 1,1-dimethylpropylsulfonyl, 1,2-dimethylpropylsulfonyl, 2,2-dimethylpropylsulfonyl, 1-ethylpropylsulfonyl, hexylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropylsulfonyl and 1-ethyl-2-methylpropylsulfonyl;

$C_1$–$C_6$-haloalkylsulfonyl: a $C_1$–$C_6$-alkylsulfonyl radical as mentioned above which is partially or fully substituted by fluorine, chlorine, bromine and/or iodine, i.e., for example, fluoromethylsulfonyl, difluoromethylsulfonyl, trifluoromethylsulfonyl, chlorodifluoromethylsulfonyl, bromodifluoromethylsulfonyl, 2-fluoroethylsulfonyl, 2-chloroethylsulfonyl, 2-bromoethylsulfonyl, 2-iodoethylsulfonyl, 2,2-difluoroethylsulfonyl, 2,2,2-trifluoroethylsulfonyl, 2-chlor-2-fluoroethylsulfonyl, 2-chloro-2,2-difluoroethylsulfonyl, 2,2-dichloro-2-fluoroethylsulfonyl, 2,2,2-trichloroethylsulfonyl, pentafluoroethylsulfonyl, 2-fluoropropylsulfonyl, 3-fluoropropylsulfonyl, 2-chloropropylsulfonyl, 3-chloropropylsulfonyl, 2-bromopropylsulfonyl, 3-bromopropylsulfonyl, 2,2-difluoropropylsulfonyl, 2,3-difluoropropylsulfonyl, 2,3-dichloropropylsulfonyl, 3,3,3-trifluoropropylsulfonyl, 3,3,3-trichloropropylsulfonyl, 2,2,3,3,3-pentafluoropropylsulfonyl, heptafluoropropylsulfonyl, 1-(fluoromethyl)-2-fluoroethylsulfonyl, 1-(chloromethyl)-2-chloroethylsulfonyl, 1-(bromomethyl)-2-bromoethylsulfonyl, 4-fluorobutylsulfonyl, 4-chlorobutylsulfonyl, 4-bromobutylsulfonyl, nonafluorobutylsulfonyl, 5-fluoropentylsulfonyl, 5-chloropentylsulfonyl, 5-bromopentylsulfonyl, 5-iodopentylsulfonyl, 6-fluorohexylsulfonyl, 6-bromohexylsulfonyl, 6-iodohexylsulfonyl or dodecafluorohexylsulfonyl;

di($C_1$–$C_4$-alkyl)amino, and the dialkylamino moieties of di($C_1$–$C_4$-alkyl)aminocarbonyl: N,N-dimethylamino, N,N-diethylamino, N,N-dipropylamino, N,N-di(1-methylethyl)amino, N,N-dibutylamino, N,N-di(1-methylpropyl)amino, N,N-di(2-methylpropyl)amino, N,N-di(1,1-dimethylethyl)amino, N-ethyl-N-methylamino, N-methyl-N-propylamino, N-methyl-N-(1-methylethyl)amino, N-butyl-N-methylamino, N-methyl-N-(1-methylpropyl)amino, N-methyl-N-(2-methylpropyl)amino, N-(1,1-dimethylethyl)-N-methylamino, N-ethyl-N-propylamino, N-ethyl-N-(1-methylethyl)amino, N-butyl-N-ethylamino, N-ethyl-N-(1-methylpropyl)amino, N-ethyl-N-(2-methylpropyl)amino, N-ethyl-N-(1,1-dimethylethyl)amino, N-(1-methylethyl)-N-propylamino, N-butyl-N-propylamino, N-(1-methylpropyl)-N-propylamino, N-(2-methylpropyl)-N-propylamino, N-(1,1-dimethylethyl)-N-propylamino, N-butyl-N-(1-methylethyl)amino, N-(1-methylethyl)-N-(1-methylpropyl)amino, N-(1-methylethyl)-N-(2-methylpropyl)amino, N-(1,1-dimethylethyl)-N-(1-methylethyl)amino, N-butyl-N-(1-methylpropyl)amino, N-butyl-N-(2-methylpropyl)amino, N-butyl-N-(1,1-dimethylethyl)amino, N-(1-methylpropyl)-N-(2-methylpropyl)amino, N-(1,1-dimethylethyl)-N-(1-methylpropyl)amino or N-(1,1-dimethylethyl)-N-(2-methylpropyl)amino;

di($C_1$–$C_6$-alkylamino) as dialkylamino moiety of di($C_1$–$C_6$-alkyl)aminocarbonyl and di($C_1$–$C_6$-alkyl) aminothiocarbonyl: N-methyl-N-pentylamino or N-methyl-N-hexylamino;

($C_1$–$C_4$-alkylamino)carbonyl: for example methylaminocarbonyl, ethylaminocarbonyl, propylaminocarbonyl, 1-methylethylaminocarbonyl, butylaminocarbonyl, 1-methylpropylaminocarbonyl, 2-methylpropylaminocarbonyl or 1,1-dimethylethylaminocarbonyl;

($C_1$–$C_6$-alkylamino)carbonyl: ($C_1$–$C_4$-alkylamino)carbonyl, as mentioned above, and also, for example, pentylaminocarbonyl, 1-methylbutylaminocarbonyl, 2-methylbutylaminocarbonyl, 3-methylbutylaminocarbonyl, 2,2-dimethylpropylaminocarbonyl, 1-ethylpropylaminocarbonyl, hexylaminocarbonyl, 1,1-dimethylpropylaminocarbonyl, 1,2-dimethylpropylaminocarbonyl, 1-methylpentylaminocarbonyl, 2-methylpentylaminocarbonyl, 3-methylpentylaminocarbonyl, 4-methylpentylaminocarbonyl, 1,1-dimethylbutylaminocarbonyl, 1,2-dimethylbutylaminocarbonyl, 1,3-dimethylbutylaminocarbonyl, 2,2-dimethylbutylaminocarbonyl, 2,3-dimethylbutylaminocarbonyl, 3,3-dimethylbutylaminocarbonyl, 1-ethylbutylaminocarbonyl, 2-ethylbutylaminocarbonyl, 1,1,2-trimethylpropylaminocarbonyl, 1,2,2-trimethylpropylaminocarbonyl, 1-ethyl-1-methylpropylaminocarbonyl or 1-ethyl-2-methylpropylaminocarbonyl;

$C_3$–$C_6$-alkenyl, and the alkenyl moieties of $C_3$–$C_6$-alkenylcarbonyl, $C_3$–$C_6$-alkenyloxycarbonyl, $C_3$–$C_6$-alkenylaminocarbonyl, N-($C_3$–$C_6$-alkenyl)-N-($C_1$–$C_6$-alkyl)aminocarbonyl: prop-1-en-1-yl, prop-2-en-1-yl, 1-methylethenyl, buten-1-yl, buten-2-yl, buten-3-yl, 1-methylprop-1-en-1-yl, 2-methylprop-1-en-1-yl, 1-methylprop-2-en-1-yl, 2-methylprop-2-en-1-yl, penten-1-yl, penten-2-yl, penten-3-yl, penten-4-yl, 1-methylbut-1-en-1-yl, 2-methylbut-1-en-1-yl, 3-methylbut-1-en-1-yl, 1-methylbut-2-en-1-yl, 2-methylbut-2-en-1-yl, 3-methylbut-2-en-1-yl, 1-methylbut-3-en-1-yl, 2-methylbut-3-en-1-yl, 3-methylbut-3-en-1-yl, 1,1-dimethylprop-2-en-1-yl, 1,2-dimethylprop-1-en-1-yl, 1,2-dimethylprop-2-en-1-yl, 1-ethylprop-1-en-2-yl, 1-ethylprop-2-en-1-yl, hex-1-en-1-yl, hex-2-en-1-yl, hex-3-en-1-yl, hex-4-en-1-yl, hex-5-en-1-yl, 1-methylpent-1-en-1-yl, 2-methylpent-1-en-1-yl, 3-methylpent-1-en-1-yl, 4-methylpent-1-en-1-yl, 1-methylpent-2-en-1-yl, 2-methylpent-2-en-1-yl, 3-methylpent-2-en-1-yl, 4-methylpent-2-en-1-yl, 1-methylpent-3-en-1-yl, 2-methylpent-3-en-1-yl, 3-methylpent-3-en-1-yl, 4-methylpent-3-en-1-yl, 1-methylpent-4-en-1-yl, 2-methylpent-4-en-1-yl, 3-methylpent-4-en-1-yl, 4-methylpent-4-en-1-yl, 1,1-dimethylbut-2-en-1-yl, 1,1-dimethylbut-3-en-1-yl, 1,2-dimethylbut-1-en-1-yl, 1,2-dimethylbut-2-en-1-yl, 1,2-dimethylbut-3-en-1-yl, 1,3-dimethylbut-1-en-1-yl, 1,3-dimethylbut-2-en-1-yl, 1,3-dimethylbut-3-en-1-yl, 2,2-dimethylbut-3-en-1-yl, 2,3-dimethylbut-1-en-1-yl, 2,3-dimethylbut-2-en-1-yl, 2,3-dimethylbut-3-en-1-yl, 3,3-dimethylbut-1-en-1-yl, 3,3-dimethylbut-2-en-1-yl, 1-ethylbut-1-en-1-yl, 1-ethylbut-2-en-1-yl, 1-ethylbut-3-en-1-yl, 2-ethylbut-1-en-1-yl, 2-ethylbut-2-en-1-yl, 2-ethylbut-3-en-1-yl, 1,1,2-trimethylprop-2-en-1-yl, 1-ethyl-1-methylprop-2-en-1-yl, 1-ethyl-2-methylprop-1-en-1-yl and 1-ethyl-2-methylprop-2-en-1-yl;

$C_2$–$C_6$-alkenyl as alkenyl moieties of $C_2$–$C_6$-alkenylcarbonyl: $C_3$–$C_6$-alkenyl as mentioned above, and also ethenyl;

$C_2$–$C_{20}$-alkenyl as alkenyl moieties of $C_2$–$C_{20}$-alkenylcarbonyl: $C_2$–$C_6$-alkenyl as mentioned above and also 8-pentadecen-1-yl, 8-heptadecen-1-yl and 8,11-heptadecadien-1-yl;

$C_3$–$C_6$-haloalkenyl: a $C_3$–$C_6$-alkenyl radical as mentioned above which is partially or fully substituted by fluorine, chlorine, bromine and/or iodine, i.e., for example, 2-chloroallyl, 3-chloroallyl, 2,3-dichloroallyl, 3,3-dichloroallyl, 2,3,3-trichloroallyl, 2,3-dichlorobut-2-enyl, 2-bromoallyl, 3-bromoallyl, 2,3-dibromoallyl, 3,3-dibromoallyl, 2,3,3-tribromoallyl or 2,3-dibromobut-2-enyl;

$C_3$–$C_6$-alkynyl, and the alkynyl moieties of $C_3$–$C_6$-alkynylcarbonyl, $C_3$–$C_6$-alkynyloxycarbonyl, $C_3$–$C_6$-alkynylaminocarbonyl, N-($C_3$–$C_6$-alkynyl)-N-($C_1$–$C_6$-alkyl)aminocarbonyl: for example propargyl, but-1-yn-3-yl, but-1-yn-4-yl, but-2-yn-1-yl, pent-1-yn-3-yl, pent-1-yn-4-yl, pent-1-yn-5-yl, pent-2-yn-1-yl, pent-2-yn-4-yl, pent-2-yn-5-yl, 3-methylbut-1-yn-3-yl, 3-methylbut-1-yn-4-yl, hex-1-yn-3-yl, hex-1-yn-4-yl, hex-1-yn-5-yl, hex-1-yn-6-yl, hex-2-yn-1-yl, hex-2-yn-4-yl, hex-2-yn-5-yl, hex-2-yn-6-yl, hex-3-yn-1-yl, hex-3-yn-2-yl, 3-methylpent-1-yn-3-yl, 3-methylpent-1-yn-4-yl, 3-methylpent-1-yn-5-yl, 4-methylpent-2-yn-4-yl or 4-methylpent-2-yn-5-yl;

$C_2$–$C_6$-alkynyl as alkynyl moiety of $C_2$–$C_6$-alkynylcarbonyl: $C_3$–$C_6$-alkynyl, as mentioned above, and also ethynyl;

$C_1$–$C_4$-alkanediyl: for example methanediyl, ethane-1,2-diyl, propane-1,3-diyl or butane-1,4-diyl;

$C_1$–$C_5$-alkanediyl: $C_1$–$C_4$-alkanediyl as mentioned above, and also pentane-1,5-diyl;

$C_3$–$C_6$-cycloalkyl, and the cycloalkyl moieties of $C_3$–$C_6$-cycloalkylcarbonyl: for example cyclopropyl, cyclobutyl, cyclopentyl or cyclohexyl;

heterocyclyl, and heterocyclyl moieties of heterocyclylcarbonyl, heterocyclyl-$C_1$–$C_6$-alkyl, heterocyclyloxycarbonyl, heterocyclyloxythiocarbonyl, heterocyclylcarbonyl-$C_1$–$C_6$-alkyl: a saturated, partially saturated or unsaturated 5- or 6-membered heterocyclic ring which contains one to four identical or different hetero atoms selected from the following group: oxygen, sulfur or nitrogen, and can be bonded via C or N, i.e. for example, C-bonded 5-membered saturated rings such as: tetrahydrofuran-2-yl, tetrahydrofuran-3-yl, tetrahydrothien-2-yl, tetrahydrothien-3-yl, tetrahydropyrrol-2-yl, tetrahydropyrrol-3-yl, tetrahydropyrazol-3-yl, tetrahydropyrazol-4-yl, tetrahydroisoxazol-3-yl, tetrahydroisoxazol-4-yl, tetrahydroisoxazol-5-yl, 1,2-oxathiolan-3-yl, 1,2-oxathiolan-4-yl, 1,2-oxathiolan-5-yl, tetrahydroisothiazol-3-yl, tetrahydroisothiazol-4-yl, tetrahydroisothiazol-5-yl, 1,2-dithiolan-3-yl, 1,2-dithiolan-4-yl, tetrahydroimidazol-2-yl, tetrahydroimidazol-4-yl, tetrahydrooxazol-2-yl, tetrahydrooxazol-4-yl, tetrahydroxazol-5-yl, tetrahydrothiazol-2-yl, tetrahydrothiazol-4-yl, tetrahydrothiazol-5-yl, 1,3-dioxolan-2-yl, 1,3-dioxolan-4-yl, 1,3-oxathiolan-2-yl, 1,3-oxathiolan-4-yl, 1,3-oxathiolan-5-yl, 1,3-dithiolan-2-yl, 1,3-dithiolan-4-yl, 1,3,2-dioxathiolan-4-yl;

C-bonded, 5-membered partially saturated rings such as: 2,3-dihydrofuran-2-yl, 2,3-dihydrofuran-3-yl, 2,5-dihydrofuran-2-yl, 2,5-dihydrofuran-3-yl, 4,5-dihydrofuran-2-yl, 4,5-dihydrofuran-3-yl, 2,3-dihydrothien-2-yl, 2,3-dihydrothien-3-yl, 2,5-dihydrothien-2-yl, 2,5-dihydrothien-3-yl, 4,5-dihydrothien-2-yl, 4,5-dihydrothien-3-yl, 2,3-dihydro-1H-pyrrol-2-yl, 2,3-dihydro-1H-pyrrol-3-yl, 2,5-dihydro-1H-pyrrol-2-yl, 2,5-dihydro-1H-pyrrol-3-yl, 4,5-dihydro-1H-pyrrol-2-yl, 4,5-dihydro-1H-pyrrol-3-yl, 3,4-dihydro-2H-pyrrol-2-yl, 3,4-dihydro-2H-pyrrol-3-yl, 3,4-dihydro-5H-pyrrol-2-yl, 3,4-dihydro-5H-pyrrol-3-yl, 4,5-dihydro-1H-pyrazol-3-yl, 4,5-dihydro-1H-pyrazol-4-yl, 4,5-dihydro-1H-pyrazol-5-yl, 2,5-dihydro-1H-pyrazol-3-yl, 2,5-dihydro-1H-pyrazol-4-yl, 2,5-dihydro-1H-pyrazol-5-yl, 4,5-dihydroisoxazol-3-yl, 4,5-dihydroisoxazol-4-yl, 4,5-dihydroisoxazol-5-yl, 2,5-dihydroisoxazol-3-yl, 2,5-dihydroisoxazol-4-yl, 2,5-dihydroisoxazol-5-yl, 2,3-dihydroisoxazol-3-yl, 2,3-dihydroisoxazol-4-yl, 2,3-dihydroisoxazol-5-yl, 4,5-dihydroisothiazol-3-yl, 4,5-dihydroisothiazol-4-yl, 4,5-dihydroisothiazol-5-yl, 2,5-dihydroisothiazol-3-yl, 2,5-dihydroisothiazol-4-yl, 2,5-dihydroisothiazol-5-yl, 2,3-dihydroisothiazol-3-yl, 2,3-dihydroisothiazol-4-yl, 2,3-dihydroisothiazol-5-yl, $\Delta^3$-1,2-dithiol-3-yl, $\Delta^3$-1,2-dithiol-4-yl, $\Delta^3$-1,2-dithiol-5-yl, 4,5-dihydro-1H-imidazol-2-yl, 4,5-dihydro-1H-imidazol-4-yl, 4,5-dihydro-1H-imidazol-5-yl, 2,5-dihydro-1H-imidazol-2-yl, 2,5-dihydro-1H-imidazol-4-yl, 2,5- dihydro-1H-imidazol-5-yl, 2,3-dihydro-1H-imidazol-2-yl, 2,3-dihydro-1H-imidazol-4-yl, 4,5-dihydrooxazol-2-yl, 4,5-dihydrooxazol-4-yl, 4,5-dihydrooxazol-5-yl, 2,5-dihydrooxazol-2-yl, 2,5-dihydrooxazol-4-yl, 2,5-dihydrooxazol-5-yl, 2,3-dihydrooxazol-2-yl, 2,3-dihydrooxazol-4-yl, 2,3-dihydrooxazol-5-yl, 4,5-dihydrothiazol-2-yl, 4,5-dihydrothiazol-4-yl, 4,5-dihydrothiazol-5-yl, 2,5-dihydrothiazol-2-yl, 2,5-dihydrothiazol-4-yl, 2,5-dihydrothiazol-5-yl, 2,3-dihydrothiazol-2-yl, 2,3-dihydrothiazol-4-yl, 2,3-dihydrothiazol-5-yl, 1,3-dioxol-2-yl, 1,3-dioxol-4-yl, 1,3-dithiol-2-yl, 1,3-Dithiol-4-yl, 1,3-oxathiol-2-yl, 1,3-oxathiol-4-yl, 1,3-oxathiol-5-yl, 1,2,3-$\Delta^2$-oxadiazolin-4-yl, 1,2,3-$\Delta^2$-oxadiazolin-5-yl, 1,2,4-$\Delta^4$-oxadiazolin-3-yl, 1,2,4-$\Delta^4$-oxadiazolin-5-yl, 1,2,4-$\Delta^2$-oxadiazolin-3-yl, 1,2,4-$\Delta^2$-oxadiazolin-5-yl, 1,2,4-$\Delta^3$-oxadiazolin-3-yl, 1,2,4-$\Delta^3$-oxadiazolin-5-yl, 1,3,4-$\Delta^2$-oxadiazolin-2-yl, 1,3,4-$\Delta^2$-oxadiazolin-5-yl, 1,3,4-$\Delta^3$-oxadiazolin-2-yl, 1,3,4-oxadiazolin-2-yl, 1,2,4-$\Delta^4$-thiadiazolin-3-yl, 1,2,4-$\Delta^4$-thiadiazolin-5-yl, 1,2,4-$\Delta^3$-thiadiazolin-3-yl, 1,2,4-$\Delta^3$-thiadiazolin-5-yl, 1,2,4-$\Delta^2$-thiadiazolin-3-yl, 1,2,4-$\Delta^2$-thiadiazolin-5-yl, 1,3,4-$\Delta^2$-thiadiazolin-2-yl, 1,3,4-$\Delta^2$-thiadiazolin-5-yl, 1,3,4-$\Delta^3$-thiadiazolin-2-yl, 1,3,4-thiadiazolin-2-yl, 1,2,3-$\Delta^2$-triazolin-4-yl, 1,2,3-$\Delta^2$-triazolin-5-yl, 1,2,4-$\Delta^2$-triazolin-3-yl, 1,2,4-$\Delta^2$-triazolin-5-yl, 1,2,4-$\Delta^3$-triazolin-3-yl, 1,2,4-$\Delta^3$-triazolin-5-yl, 1,2,4-$\Delta^1$-triazolin-2-yl, 1,2,4-triazolin-3-yl, 3H-1,2,4-dithiazol-5-yl, 2H-1,3,4-dithiazol-5-yl, 2H-1,3,4-oxathiazol-5-yl;

C-bonded, 5-membered unsaturated rings such as:
2-furyl, 3-furyl, 2-thienyl, 3-thienyl, pyrrol-2-yl, pyrrol-3-yl, pyrazol-3-yl, pyrazol-4-yl, isoxazol-3-yl, isoxazol-4-yl, isoxazol-5-yl, isothiazol-3-yl, isothiazol-4-yl, isothiazol-5-yl, imidazol-2-yl, imidazol-4-yl, oxazol-2-yl, oxazol-4-yl, oxazol-5-yl, thiazol-2-yl, thiazol-4-yl, thiazol-5-yl, 1,2,3-oxadiazol-4-yl, 1,2,3-oxadiazol-5-yl, 1,2,4-oxadiazol-3-yl, 1,2,4-oxadiazol-5-yl, 1,3,4-oxadiazol-2-yl, 1,2,3-thiadiazol-4-yl, 1,2,3-thiadiazol-5-yl, 1,2,4-thiadiazol-3-yl, 1,2,4-thiadiazol-5-yl, 1,3,4-thiadiazolyl-2-yl, 1,2,3-triazol-4-yl, 1,2,4-triazol-3-yl, tetrazol-5-yl;

C-bonded, 6-membered saturated rings, such as:
tetrahydropyran-2-yl, tetrahydropyran-3-yl, tetrahydropyran-4-yl, piperidin-2-yl, piperidin-3-yl, piperidin-4-yl, tetrahydrothiopyran-2-yl, tetrahydrothiopyran-3-yl, tetrahydrothiopyran-4-yl, 1,3-dioxan-2-yl, 1,3-dioxan-4-yl, 1,3-dioxan-5-yl, 1,4-dioxan-2-yl, 1,3-dithian-2-yl, 1,3-dithian-4-yl, 1,3-dithian-5-yl, 1,4-dithian-2-yl, 1,3-oxathian-2-yl, 1,3-oxathian-4-yl, 1,3-oxathian-5-yl, 1,3-oxathian-6-yl, 1,4-oxathian-2-yl, 1,4-oxathian-3-yl, 1,2-dithian-3-yl, 1,2-dithian-4-yl, hexahydropyrimidin-2-yl, hexahydropyrimidin-4-yl, hexahydropyrimidin-5-yl, hexahydropyrazin-2-yl, hexahydropyridazin-3-yl, hexahydropyridazin-4-yl, tetrahydro-1,3-oxazin-2-yl, tetrahydro-1,3-oxazin-4-yl, tetrahydro-1,3-oxazin-5-yl, tetrahydro-1,3-oxazin-6-yl, tetrahydro-1,3-thiazin-2-yl, tetrahydro-1,3-thiazin-4-yl, tetrahydro-1,3-thiazin-5-yl, tetrahydro-1,3-thiazin-6-yl, tetrahydro-1,4-thiazin-2-yl, tetrahydro-1,4-thiazin-3-yl, tetrahydro-1,4-oxazin-2-yl, tetrahydro-1,4-oxazin-3-yl, tetrahydro-1,2-oxazin-3-yl, tetrahydro-1,2-oxazin-4-yl, tetrahydro-1,2-oxazin-5-yl, tetrahydro-1,2-oxazin-6-yl;

C-bonded, 6-membered partially saturated rings such as:
2H-3,4-dihydropyran-6-yl, 2H-3,4-dihydropyran-5-yl, 2H-3,4-dihydropyran-4-yl, 2H-3,4-dihydropyran-3-yl, 2H-3,4-dihydropyran-2-yl, 2H-3,4-dihydropyran-6-yl, 2H-3,4-dihydrothiopyran-5-yl, 2H-3,4-dihydrothiopyran-4-yl, 2H-3,4-dihydrothiopyran-3-yl, 2H-3,4-dihydropyran-2-yl, 1,2,3,4-tetrahydropyridin-6-yl, 1,2,3,4-tetrahydropyridin-5-yl, 1,2,3,4-tetrahydropyridin-4-yl, 1,2,3,4-tetrahydropyridin-3-yl, 1,2,3,4-tetrahydropyridin-2-yl, 2H-5,6-dihydropyran-2-yl, 2H-5,6-dihydropyran-3-yl, 2H-5,6-dihydropyran-4-yl, 2H-5,6-dihydropyran-5-yl, 2H-5,6-dihydropyran-6-yl, 2H-5,6-dihydrothiopyran-2-yl, 2H-5,6-dihydrothiopyran-3-yl, 2H-5,6-dihydrothiopyran-4-yl, 2H-5,6-dihydrothiopyran-5-yl, 2H-5,6-dihydrothiopyran-6-yl, 1,2,5,6-tetrahydropyridin-2-yl, 1,2,5,6-tetrahydropyridin-3-yl, 1,2,5,6-tetrahydropyridin-4-yl, 1,2,5,6-tetrahydropyridin-5-yl, 1,2,5,6-tetrahydropyridin-6-yl, 2,3,4,5-tetrahydropyridin-2-yl, 2,3,4,5-tetrahydropyridin-3-yl, 2,3,4,5-tetrahydropyridin-4-yl, 2,3,4,5-tetrahydropyridin-5-yl, 2,3,4,5-tetrahydropyridin-6-yl, 4H-pyran-2-yl, 4H-pyran-3-yl, 4H-pyran-4-yl, 4H-thiopyran-2-yl, 4H-thiopyran-3-yl, 4H-thiopyran-4-yl, 1,4-dihydropyridin-2-yl, 1,4-dihydropyridin-3-yl, 1,4-dihydropyridin-4-yl, 2H-pyran-2-yl, 2H-pyran-3-yl, 2H-pyran-4-yl, 2H-pyran-5-yl, 2H-pyran-6-yl, 2H-thiopyran-2-yl, 2H-thiopyran-3-yl, 2H-thiopyran-4-yl, 2H-thiopyran-5-yl, 2H-thiopyran-6-yl, 1,2-dihydropyridin-2-yl, 1,2-dihydropyridin-3-yl, 1,2-dihydropyridin-4-yl, 1,2-dihydropyridin-5-yl, 1,2-dihydropyridin-6-yl, 3,4-dihydropyridin-2-yl, 3,4-dihydropyridin-3-yl, 3,4-dihydropyridin-4-yl, 3,4-dihydropyridin-5-yl, 3,4-dihydropyridin-6-yl, 2,5-dihydropyridin-2-yl, 2,5-dihydropyridin-3-yl, 2,5-dihydropyridin-4-yl, 2,5-dihydropyridin-5-yl, 2,5-dihydropyridin-6-yl, 2,3-dihydropyridin-2-yl, 2,3-dihydropyridin-3-yl, 2,3-dihydropyridin-4-yl, 2,3-dihydropyridin-5-yl, 2,3-dihydropyridin-6-yl, 2H-5,6-dihydro-1,2-oxazin-3-yl, 2H-5,6-dihydro-1,2-oxazin-4-yl, 2H-5,6-dihydro-1,2-oxazin-5-yl, 2H-5,6-dihydro-1,2-oxazin-6-yl, 2H-5,6-dihydro-1,2-thiazin-3-yl, 2H-5,6-dihydro-1,2-thiazin-4-yl, 2H-5,6-dihydro-1,2-thiazin-5-yl, 2H-5,6-dihydro-1,2-thiazin-6-yl, 4H-5,6-dihydro-1,2-oxazin-3-yl, 4H-5,6-dihydro-1,2-oxazin-4-yl, 4H-5,6-dihydro-1,2-oxazin-5-yl, 4H-5,6-dihydro-1,2-oxazin-6-yl, 4H-5,6-dihydro-1,2-thiazin-3-yl, 4H-5,6-dihydro-1,2-thiazin-4-yl, 4H-5,6-dihydro-1,2-thiazin-5-yl, 4H-5,6-dihydro-1,2-thiazin-6-yl, 2H-3,6-dihydro-1,2-oxazin-3-yl, 2H-3,6-dihydro-1,2-oxazin-4-yl, 2H-3,6-dihydro-1,2-oxazin-5-yl, 2H-3,6-dihydro-1,2-oxazin-6-yl, 2H-3,6-dihydro-1,2-thiazin-3-yl, 2H-3,6-dihydro-1,2-thiazin-4-yl, 2H-3,6-dihydro-1,2-thiazin-5-yl, 2H-3,6-dihydro-1,2-thiazin-6-yl, 2H-3,4-dihydro-1,2-oxazin-3-yl, 2H-3,4-dihydro-1,2-oxazin-4-yl, 2H-3,4-dihydro-1,2-oxazin-5-yl, 2H-3,4-dihydro-1,2-oxazin-6-yl, 2H-3,4-dihydro-1,2-thiazin-3-yl, 2H-3,4-dihydro-1,2-thiazin-4-yl, 2H-3,4-dihydro-1,2-thiazin-5-yl, 2H-3,4-dihydro-1,2-thiazin-6-yl, 2,3,4,5-tetrahydropyridazin-3-yl, 2,3,4,5-tetrahydropyridazin-4-yl, 2,3,4,5-tetrahydropyridazin-5-yl, 2,3,4,5-tetrahydropyridazin-6-yl, 3,4,5,6-tetrahydropyridazin-3-yl, 3,4,5,6- tetrahydropyridazin-4-yl, 1,2,5,6-tetrahydropyridazin-3-yl, 1,2,5,6-tetrahydropyridazin-4-yl, 1,2,5,6-tetrahydropyridazin-5-yl, 1,2,5,6-tetrahydropyridazin-6-yl, 1,2,3,6-tetrahydropyridazin-3-yl, 1,2,3,6-tetrahydropyridazin-4-yl, 4H-5,6-dihydro-1,3-oxazin-2-yl, 4H-5,6-dihydro-1,3-oxazin-4-yl, 4H-5,6-dihydro-1,3-oxazin-5-yl, 4H-5,6-dihydro-1,3-oxazin-6-yl, 4H-5,6-dihydro-1,3-thiazin-2-yl, 4H-5,6-dihydro-1,3-thiazin-4-yl, 4H-5,6-dihydro-1,3-thiazin-5-yl, 4H-5,6-dihydro-1,3-thiazin-6-yl, 3,4,5,6-tetrahydropyrimidin-2-yl, 3,4,5,6-tetrahydropyrimidin-4-yl, 3,4,5,6-tetrahydropyrimidin-5-yl, 3,4,5,6-tetrahydropyrimidin-6-yl, 1,2,3,4-tetrahydropyrazin-2-yl, 1,2,3,4-tetrahydropyrazin-5-yl, 1,2,3,4-tetrahydropyrimidin-2-yl, 1,2,3,4-tetrahydropyrimidin-4-yl, 1,2,3,4-tetrahydropyrimidin-5-yl, 1,2,3,4-tetrahydropyrimidin-6-yl, 2,3-dihydro-1,4-oxazin-2-yl, 2,3-dihydro-1,4-thiazin-3-yl, 2,3-dihydro-1,4-thiazin-5-yl, 2,3-dihydro-1,4-thiazin-6-yl, 2H-1,2-oxazin-3-yl, 2H-1,2-oxazin-4-yl, 2H-1,2-oxazin-5-yl, 2H-1,2-oxazin-6-yl, 2H-1,2-thiazin-3-yl, 2H-1,2-thiazin-4-yl, 2H-1,2-thiazin-5-yl, 2H-1,2-thiazin-6-yl, 4H-1,2-oxazin-3-yl, 4H-1,2-oxazin-4-yl, 4H-1,2-oxazin-5-yl, 4H-1,2-oxazin-6-yl, 4H-1,2-thiazin-3-yl, 4H-1,2-thiazin-4-yl, 4H-1,2-thiazin-5-yl, 4H-1,2-thiazin-6-yl, 6H-1,2-oxazin-3-yl, 6H-1,2-oxazin-4-yl, 6H-1,2-oxazin-5-yl, 6H-1,2-oxazin-6-yl, 6H-1,2-thiazin-3-yl, 6H-1,2-thiazin-4-yl, 6H-1,2-thiazin-5-yl, 6H-1,2-thiazin-6-yl, 2H-1,3-oxazin-2-yl, 2H-1,3-oxazin-4-yl, 2H-1,3-oxazin-5-yl, 2H-1,3-oxazin-6-yl, 2H-1,3-thiazin-2-yl, 2H-1,3-thiazin-4-yl, 2H-1,3-thiazin-5-yl, 2H-1,3-thiazin-6-yl, 4H-1,3-oxazin-2-yl, 4H-1,3-oxazin-4-yl, 4H-1,3-oxazin-5-yl, 4H-1,3-oxazin-6-yl, 4H-1,3-thiazin-2-yl, 4H-1,3-thiazin-4-yl, 4H-1,3-thiazin-5-yl, 4H-1,3-thiazin-6-yl, 6H-1,3-oxazin-2-yl, 6H-1,3-oxazin-4-yl, 6H-1,3-oxazin-5-yl, 6H-1,3-oxazin-6-yl, 6H-1,3-thiazin-2-yl, 6H-1,3-thiazin-4-yl, 6H-1,3-thiazin-5-yl, 6H-1,3-thiazin-6-yl, 2H-1,4-oxazin-2-yl, 2H-1,4-oxazin-3-yl, 2H-1,4-oxazin-5-yl, 2H-1,4-oxazin-6-yl, 2H-1,4-thiazin-2-yl, 2H-1,4-thiazin-3-yl, 2H-1,4-thiazin-5-yl, 2H-1,4-thiazin-6-yl, 4H-1,4-oxazin-2-yl, 4H-1,4-oxazin-3-yl, 4H-1,4-thiazin-2-yl, 4H-1,4-thiazin-3-yl, 1,4-dihydropyridazin-3-yl, 1,4-dihydropyridazin-4-yl, 1,4-dihydropyridazin-5-yl, 1,4-dihydropyridazin-6-yl, 1,4-dihydropyrazin-2-yl, 1,2-dihydropyrazin-2-yl, 1,2-dihydropyrazin-3-yl, 1,2-dihydropyrazin-5-yl, 1,2-dihydropyrazin-6-yl, 1,4-dihydropyrimidin-2-yl, 1,4-dihydropyrimidin-4-yl, 1,4-dihydropyrimidin-5-yl, 1,4-dihydropyrimidin-6-yl, 3,4-dihydropyrimidin-2-yl, 3,4-dihydropyrimidin-4-yl, 3,4-dihydropyrimidin-5-yl or 3,4-dihydropyrimidin-6-yl;

C-bonded, 6-membered unsaturated rings such as:
pyridin-2-yl, pyridin-3-yl, pyridin-4-yl, pyridazin-3-yl, pyridazin-4-yl, pyrimidin-2-yl, pyrimidin-4-yl, pyrimidin-5-yl, pyrazin-2-yl, 1,3,5-triazin-2-yl, 1,2,4-triazin-3-yl, 1,2,4-triazin-5-yl, 1,2,4-triazin-6-yl, 1,2,4,5-tetrazin-3-yl;

N-bonded, 5-membered saturated rings such as:
tetrahydropyrrol-1-yl, tetrahydropyrazol-1-yl, tetrahydroisoxazol-2-yl, tetrahydroisothiazol-2-yl, tetrahydroimidazol-1-yl, tetrahydrooxazol-3-yl, tetrahydrothiazol-3-yl;

N-bonded, 5-membered partially saturated rings such as:
2,3-dihydro-1H-pyrrol-1-yl, 2,5-dihydro-1H-pyrrol-1-yl, 4,5-dihydro-1H-pyrazol-1-yl, 2,5-dihydro-1H-pyrazol-1-yl, 2,3-dihydro-1H-pyrazol-1-yl, 2,5-dihydroisoxazol-2-yl, 2,3-dihydroisoxazol-2-yl, 2,5-dihydroisothiazol-2-yl, 2,3-dihydroisothiazol-2-yl, 4,5-dihydro-1H-imidazol-1-yl, 2,5-dihydro-1H-imidazol-1-yl, 2,3-dihydro-1H-imidazol-1-yl, 2,3-dihydrooxazol-3-yl, 2,3-dihydrothiazol-3-yl, 1,2,4-$\Delta^4$-oxadiazolin-2-yl, 1,2,4-$\Delta^2$-oxadiazolin-4-yl, 1,2,4-$\Delta^3$-oxadiazolin-2-yl, 1,3,4-$\Delta^2$-oxadiazolin-4-yl, 1,2,4-$\Delta^5$-thiadiazolin-2-yl, 1,2,4-$\Delta^3$-thiadiazolin-2-yl, 1,2,4-$\Delta^2$-thiadiazolin-4-yl, 1,3,4-$\Delta^2$-thiadiazolin-4-yl, 1,2,3-$\Delta^2$-triazolin-1-yl, 1,2,4-$\Delta^2$-triazolin-1-yl, 1,2,4-$\Delta^2$-triazolin-4-yl, 1,2,4-$\Delta^3$-triazolin-1-yl, 1,2,4-$\Delta^1$-triazolin-4-yl;

N-bonded, 5-membered unsaturated rings such as:
pyrrol-1-yl, pyrazol-1-yl, imidazol-1-yl, 1,2,3-triazol-1-yl, 1,2,4-triazol-1-yl, tetrazol-1-yl;

N-bonded, 6-membered saturated rings such as:
piperidin-1-yl, hexahydropyrimidin-1-yl, hexahydropyrazin-1-yl, hexahydropyridazin-1-yl, tetrahydro-1,3-oxazin-3-yl, tetrahydro-1,3-thiazin-3-yl, tetrahydro-1,4-thiazin-4-yl, tetrahydro-1,4-oxazin-4-yl, tetrahydro-1,2-oxazin-2-yl;

and N-bonded, 6-membered partially saturated rings such as:
1,2,3,4-tetrahydropyridin-1-yl, 1,2,5,6-tetrahydropyridin-1-yl, 1,4-dihydropyridin-1-yl, 1,2-dihydropyridin-1-yl, 2H-5,6-dihydro-1,2-oxazin-2-yl, 2H-5,6-dihydro-1,2-thiazin-2-yl, 2H-3,6-dihydro-1,2-oxazin-2-yl, 2H-3,6-dihydro-1,2-thiazin-2-yl, 2H-3,4-dihydro-1,2-oxazin-2-yl, 2H-3,4-dihydro-1,2-thiazin-2-yl, 2,3,4,5-tetrahydropyridazin-2-yl, 1,2,5,6-tetrahydropyridazin-1-yl, 1,2,5,6-tetrahydropyridazin-2-yl, 1,2,3,6-tetrahydropyridazin-1-yl, 3,4,5,6-tetrahydropyrimidin-3-yl, 1,2,3,4-tetrahydropyrazin-1-yl, 1,2,3,4-tetrahydropyrimidin-1-yl, 1,2,3,4-tetrahydropyrimidin-3-yl, 2,3-dihydro-1,4-thiazin-4-yl, 2H-1,2-oxazin-2-yl, 2H-1,2-thiazin-2-yl, 4H-1,4-oxazin-4-yl, 4H-1,4-thiazin-4-yl, 1,4-dihydropyridazin-1-yl, 1,4-dihydropyrazin-1-yl, 1,2-dihydropyrazin-1-yl, 1,4-dihydropyrimidin-1-yl or 3,4-dihydropyrimidin-3-yl;

where, if appropriate, the sulfur of the heterocycles mentioned may be oxidized to S=O or S(=O)$_2$
and where a bicyclic ring system may be formed together with a fused phenyl ring or a $C_3$–$C_6$-carboxycycle or a further 5- to 6-membered heterocycle.

The phenyl rings or heterocyclyl radicals are preferably unsubstituted or carry one, two or three halogen atoms and/or one nitro group, one cyano group, one or two methyl, trifluoromethyl, methoxy or trifluoromethoxy groups.

In the formula I, $R^1$ is preferably $C_1$–$C_6$-alkyl, $C_1$–$C_6$-haloalkyl, $C_1$–$C_6$-alkoxy; in particular $C_1$–$C_6$-alkyl; particularly preferably $C_1$–$C_4$-alkyl, most preferably methyl;

$R^2$ is preferably $C_1$–$C_6$-haloalkyl, $C_1$–$C_6$-alkylsulfonyl, halogen or nitro; in particular $C_1$–$C_6$-haloalkyl, preferably difluoromethyl or trifluoromethyl, $C_1$–$C_6$-alkylsulfonyl or halogen, preferably fluorine or chlorine; particularly preferably $C_1$–$C_4$-alkylsulfonyl, most preferably methylsulfonyl or ethylsulfonyl;

$R^3$ is preferably hydrogen, $C_1$–$C_4$-alkyl or halogen; in particular hydrogen, methyl or chlorine; particularly preferably hydrogen;

$R^4$ is preferably $C_1$–$C_2$-haloalkyl; in particular fluoromethyl, chloromethyl, bromomethyl, difluoromethyl, trifluoromethyl, 1-chloro-1-ethyl, 1-fluoro-1-ethyl or pentafluoromethyl; particularly preferably fluoromethyl, chloromethyl, bromomethyl, difluoromethyl and trifluoromethy;

$R^5$ is preferably hydrogen, $C_1$–$C_2$-alkyl, $C_1$–$C_2$-haloalkyl; in particular hydrogen, methyl, chloromethyl or trifluoromethyl; particularly preferably hydrogen, methyl or chloromethyl;

$R^6$ is preferably hydrogen or $C_1$–$C_4$-alkyl; in particular hydrogen or methyl;

$R^7$ is preferably hydrogen or $C_1$–$C_4$-alkyl; in particular hydrogen or methyl; particularly preferably hydrogen;

$R^8$ is preferably hydroxyl, $OR^{15}$, $SR^{15}$, $SOR^{16}$ or $SO_2R^{16}$; in particular hydroxyl, $OR^{15}$ or $SR^{15}$; particularly preferably hydroxyl;

$R^9$, $R^{13}$ independently of one another are preferably hydrogen, $C_1$–$C_4$-alkyl or $C_1$–$C_4$-alkylthio; in particular hydrogen, methyl or methylthio; particularly preferably hydrogen;

$R^{10}$, $R^{12}$, $R^{14}$ independently of one another are preferably hydrogen or methyl;

$R^{11}$ is preferably hydrogen, hydroxyl, $C_1$–$C_6$-alkyl or di($C_1$–$C_6$-alkoxy)methyl; in particular hydrogen or $C_1$–$C_4$-alkyl; or $R^9$ and $R^{10}$ or $R^{10}$ and $R^{11}$ or $R^{11}$ and $R^{14}$ or $R^{10}$ and $R^{14}$ or $R^{13}$ and $R^{14}$ together are preferably $C_1$–$C_5$-alkanediyl which may carry one, two or three substituents selected from the group consisting of halogen, cyano, $C_1$–$C_4$-alkyl, $C_1$–$C_4$-haloalkyl and $C_1$–$C_4$-alkoxycarbonyl;

$R^9$ and $R^{10}$ or $R^{10}$ and $R^{14}$ together are in particular $C_1$–$C_5$-alkanediyl; or $R^{11}$ and $R^{12}$ together are preferably an oxygen atom;

$R^{15}$ is preferably $C_1$–$C_6$-alkyl, $C_1$–$C_{20}$-alkylcarbonyl, preferably $C_1$–$C_6$-alkylcarbonyl, $C_1$–$C_6$-alkoxycarbonyl, $C_1$–$C_6$-alkylthiocarbonyl, where the alkyl and alkoxy radicals mentioned may be partially or fully halogenated and/or may carry one, two or three substituents selected from the group consisting of cyano, $C_1$–$C_4$-alkoxy, $C_1$–$C_4$-alkylthio, $C_1$–$C_4$-alkylcarbonyl, $C_1$–$C_4$-alkoxycarbonyl and $C_3$–$C_6$-cycloalkyl; phenyl, phenyl-$C_1$–$C_4$-alkyl, phenylcarbonyl-$C_1$–$C_4$-alkyl, phenylcarbonyl, phenoxycarbonyl, heterocyclyl, heterocyclyl-$C_1$–$C_4$-alkyl, heterocyclylcarbonyl-$C_1$–$C_4$-alkyl, heterocyclyloxycarbonyl, where the phenyl or heterocyclyl radical of the radicals mentioned may be partially or fully halogenated and/or may carry one, two or three substituents selected from the group consisting of nitro, cyano, $C_1$–$C_4$-alkyl, $C_1$–$C_4$-haloalkyl, $C_1$–$C_4$-alkoxy and $C_1$–$C_4$-haloalkoxy;

$R^{16}$ is preferably $C_1$–$C_6$-alkyl which may be partially or fully halogenated and/or may carry one, two or three substituents selected from the group consisting of cyano, $C_1$–$C_4$-alkoxy, $C_1$–$C_4$-alkylthio, $C_1$–$C_4$-alkylcarbonyl, $C_1$–$C_4$-alkoxycarbonyl and $C_3$–$C_6$-cycloalkyl; phenyl, phenyl-$C_1$–$C_4$-alkyl, phenylcarbonyl-$C_1$–$C_4$-alkyl, heterocyclyl, heterocyclyl-$C_1$–$C_4$-alkyl or heterocyclylcarbonyl-$C_1$–$C_4$-alkyl, where the phenyl or heterocyclyl radical of the radicals mentioned may be partially or fully halogenated and/or may carry one, two or three substituents selected from the group consisting of nitro, cyano, $C_1$–$C_4$-alkyl, $C_1$–$C_4$-haloalkyl, $C_1$–$C_4$-alkoxy and $C_1$–$C_4$-haloalkoxy.

Particular preference is given to haloalkyl-substituted 3-(4,5-dihydroisoxazol-3-yl)benzoylcyclohexenones of the formula I in which $R^4$ is fluoromethyl, chloromethyl, bromomethyl, difluoromethyl, trifluoromethyl, 1-chloro-1-ethyl, 1-fluoro-1-ethyl or pentafluoroethyl; in particular fluoromethyl, ohloromethyl, bromomethyl, difluoromethyl or trifluoromethyl.

Extraordinary preference is given to haloalkyl-substituted 3-(4,5-dihydroisoxazol-3-yl)benzoylcyclohexenones of the formula I in which $R^1$ is $C_1$–$C_4$-alkyl;

$R^2$ is $C_1$–$C_6$-haloalkyl, $C_1$–$C_6$-alkylsulfonyl, halogen or nitro; and $R^3$ is hydrogen.

Particular preference is furthermore given to haloalkyl-substituted 3-(4,5-dihydroisoxazol-3-yl)benzoylcyclohexenones of the formula I in which $R^9$ and $R^{13}$ independently of one another are hydrogen, $C_1$–$C_4$-alkyl or $C_1$–$C_4$-alkylthio;

$R^{10}$, $R^{12}$, $R^{14}$ independently of one another are hydrogen or methyl and $R^{11}$ is hydrogen, hydroxyl, $C_1$–$C_6$-alkyl or di($C_1$–$C_6$-alkoxy)methyl; or $R^9$ and $R^{10}$ or $R^{10}$ and $R^{11}$ or $R^{11}$ and $R^{14}$ or $R^{10}$ and $R^{14}$ or $R^{13}$ and $R^{14}$ together are $C_1$–$C_5$-alkanediyl which may carry one, two or three substituents selected from the group consisting of halogen, cyano, $C_1$–$C_4$-alkyl, $C_1$–$C_4$-haloalkyl and $C_1$–$C_4$-alkoxycarbonyl; or $R^{11}$ and $R^{12}$ together are an oxygen atom. Particular preference is furthermore given to haloalkyl-substituted 3-(4,5-dihydroisoxazol-3-yl) benzoylcyclohexenones of the formula I in which $R^8$ is hydroxyl, $OR^{15}$ or $SR^{15}$; and $R^{15}$ is $C_1$–$C_6$-alkyl, $C_1$–$C_{20}$-alkylcarbonyl, $C_1$–$C_6$-alkoxycarbonyl, $C_1$–$C_6$-alkylthiocarbonyl, where the alkyl and alkoxy radicals may be partially or fully halogenated and/or may carry one, two or three substituents selected from the group consisting of cyano, $C_1$–$C_4$-alkoxy, $C_1$–$C_4$-alkylthio, $C_1$–$C_4$-alkylcarbonyl, $C_1$–$C_4$-alkoxycarbonyl and $C_3$–$C_6$-cycloalkyl; phenyl, phenyl-$C_1$–$C_4$-alkyl, phenylcarbonyl-$C_1$–$C_4$-alkyl, phenylcarbonyl, phenoxycarbonyl, heterocyclyl, heterocyclyl-$C_1$–$C_4$-alkyl, heterocyclylcarbonyl-$C_1$–$C_4$-alkyl, heterocyclyloxycarbonyl, where the phenyl or heterocyclyl radical of the radicals mentioned may be partially or fully halogenated and/or may carry one, two or three substituents selected from the group consisting of nitro, cyano, $C_1$–$C_4$-alkyl, $C_1$–$C_4$-haloalkyl, $C_1$–$C_4$-alkoxy and $C_1$–$C_4$-haloalkoxy.

Heterocyclyl is preferably a C-bonded 5-membered unsaturated ring or a C-bonded 6-membered unsaturated ring, in particular pyridin-2-yl or pyridin-3-yl.

Extraordinary preference is given to the compounds of the formula Ia1 ($\equiv$I where $R^3$, $R^9$—$R^{14}$=H, $R^8$=OH), in particular to the compounds Ia1.1 to Ia1.72 of Table 1, where the definitions of the radicals $R^1$ to $R^{14}$ are of particular importance for the compounds according to the invention not only in combination with one another but in each case also on their own.

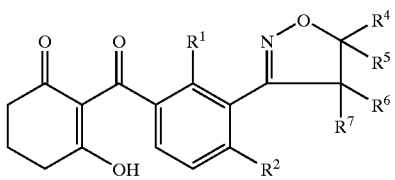

TABLE 1

| No. | $R^1$ | $R^2$ | $R^4$ | $R^5$ | $R^6$ | $R^7$ |
|---|---|---|---|---|---|---|
| Ia1.1 | $CH_3$ | $SO_2CH_3$ | $CH_2F$ | H | H | H |
| Ia1.2 | $CH_3$ | $SO_2CH_3$ | $CH_2F$ | $CH_2F$ | H | H |
| Ia1.3 | $CH_3$ | $SO_2CH_3$ | $CH_2F$ | $CH_3$ | H | H |
| Ia1.4 | $CH_3$ | $SO_2CH_3$ | $CH_2Cl$ | H | H | H |
| Ia1.5 | $CH_3$ | $SO_2CH_3$ | $CH_2Cl$ | $CH_2Cl$ | H | H |
| Ia1.6 | $CH_3$ | $SO_2CH_3$ | $CH_2Cl$ | $CH_3$ | H | H |
| Ia1.7 | $CH_3$ | $SO_2CH_3$ | $CH_2Br$ | H | H | H |
| Ia1.8 | $CH_3$ | $SO_2CH_3$ | $CH_2Br$ | $CH_3$ | H | H |
| Ia1.9 | $CH_3$ | $SO_2CH_3$ | $CHF_2$ | H | H | H |
| Ia1.10 | $CH_3$ | $SO_2CH_3$ | $CHF_2$ | $CH_3$ | H | H |
| Ia1.11 | $CH_3$ | $SO_2CH_3$ | $CHF_2$ | $CHF_2$ | H | H |
| Ia1.12 | $CH_3$ | $SO_2CH_3$ | $CF_3$ | H | H | H |
| Ia1.13 | $CH_3$ | $SO_2CH_3$ | $CF_3$ | $CF_3$ | H | H |
| Ia1.14 | $CH_3$ | $SO_2CH_3$ | $CF_3$ | $CH_3$ | H | H |
| Ia1.15 | $CH_3$ | $SO_2CH_3$ | $CHClCH_3$ | H | H | H |
| Ia1.16 | $CH_3$ | $SO_2CH_3$ | $CHBrCH_3$ | H | H | H |
| Ia1.17 | $CH_3$ | $SO_2CH_3$ | $CHFCH_3$ | H | H | H |
| Ia1.18 | $CH_3$ | $SO_2CH_3$ | $CF_2CF_3$ | H | H | H |
| Ia1.19 | $CH_3$ | $CF_3$ | $CH_2F$ | H | H | H |
| Ia1.20 | $CH_3$ | $CF_3$ | $CH_2F$ | $CH_2F$ | H | H |
| Ia1.21 | $CH_3$ | $CF_3$ | $CH_2F$ | $CH_3$ | H | H |
| Ia1.22 | $CH_3$ | $CF_3$ | $CH_2Cl$ | H | H | H |
| Ia1.23 | $CH_3$ | $CF_3$ | $CH_2Cl$ | $CH_2Cl$ | H | H |
| Ia1.24 | $CH_3$ | $CF_3$ | $CH_2Cl$ | $CH_3$ | H | H |
| Ia1.25 | $CH_3$ | $CF_3$ | $CH_2Br$ | H | H | H |
| Ia1.26 | $CH_3$ | $CF_3$ | $CH_2Br$ | $CH_3$ | H | H |
| Ia1.27 | $CH_3$ | $CF_3$ | $CHF_2$ | H | H | H |
| Ia1.28 | $CH_3$ | $CF_3$ | $CHF_2$ | $CH_3$ | H | H |
| Ia1.29 | $CH_3$ | $CF_3$ | $CHF_2$ | $CHF_2$ | H | H |
| Ia1.30 | $CH_3$ | $CF_3$ | $CF_3$ | H | H | H |
| Ia1.31 | $CH_3$ | $CF_3$ | $CF_3$ | $CF_3$ | H | H |
| Ia1.32 | $CH_3$ | $CF_3$ | $CF_3$ | $CH_3$ | H | H |
| Ia1.33 | $CH_3$ | $CF_3$ | $CHClCH_3$ | H | H | H |
| Ia1.34 | $CH_3$ | $CF_3$ | $CHBrCH_3$ | H | H | H |
| Ia1.35 | $CH_3$ | $CF_3$ | $CHFCH_3$ | H | H | H |
| Ia1.36 | $CH_3$ | $CF_3$ | $CF_2CF_3$ | H | H | H |
| Ia1.37 | $CH_2CH_3$ | $SO_2CH_3$ | $CH_2F$ | H | H | H |
| Ia1.38 | $CH_2CH_3$ | $SO_2CH_3$ | $CH_2F$ | $CH_2F$ | H | H |
| Ia1.39 | $CH_2CH_3$ | $SO_2CH_3$ | $CH_2F$ | $CH_3$ | H | H |
| Ia1.40 | $CH_2CH_3$ | $SO_2CH_3$ | $CH_2Cl$ | H | H | H |
| Ia1.41 | $CH_2CH_3$ | $SO_2CH_3$ | $CH_2Cl$ | $CH_2Cl$ | H | H |
| Ia1.42 | $CH_2CH_3$ | $SO_2CH_3$ | $CH_2Cl$ | $CH_3$ | H | H |
| Ia1.43 | $CH_2CH_3$ | $SO_2CH_3$ | $CH_2Br$ | H | H | H |
| Ia1.44 | $CH_2CH_3$ | $SO_2CH_3$ | $CH_2Br$ | $CH_3$ | H | H |
| Ia1.45 | $CH_2CH_3$ | $SO_2CH_3$ | $CHF_2$ | H | H | H |
| Ia1.46 | $CH_2CH_3$ | $SO_2CH_3$ | $CHF_2$ | $CH_3$ | H | H |
| Ia1.47 | $CH_2CH_3$ | $SO_2CH_3$ | $CHF_2$ | $CHF_2$ | H | H |
| Ia1.48 | $CH_2CH_3$ | $SO_2CH_3$ | $CF_3$ | H | H | H |
| Ia1.49 | $CH_2CH_3$ | $SO_2CH_3$ | $CF_3$ | $CF_3$ | H | H |
| Ia1.50 | $CH_2CH_3$ | $SO_2CH_3$ | $CF_3$ | $CH_3$ | H | H |
| Ia1.51 | $CH_2CH_3$ | $SO_2CH_3$ | $CHClCH_3$ | H | H | H |
| Ia1.52 | $CH_2CH_3$ | $SO_2CH_3$ | $CHBrCH_3$ | H | H | H |
| Ia1.53 | $CH_2CH_3$ | $SO_2CH_3$ | $CHFCH_3$ | H | H | H |
| Ia1.54 | $CH_2CH_3$ | $SO_2CH_3$ | $CF_2CF_3$ | H | H | H |
| Ia1.55 | $CH_3$ | $SO_2CH_2CH_3$ | $CH_2F$ | H | H | H |
| Ia1.56 | $CH_3$ | $SO_2CH_2CH_3$ | $CH_2F$ | $CH_2F$ | H | H |
| Ia1.57 | $CH_3$ | $SO_2CH_2CH_3$ | $CH_2F$ | $CH_3$ | H | H |
| Ia1.58 | $CH_3$ | $SO_2CH_2CH_3$ | $CH_2Cl$ | H | H | H |
| Ia1.59 | $CH_3$ | $SO_2CH_2CH_3$ | $CH_2Cl$ | $CH_2Cl$ | H | H |
| Ia1.60 | $CH_3$ | $SO_2CH_2CH_3$ | $CH_2Cl$ | $CH_3$ | H | H |
| Ia1.61 | $CH_3$ | $SO_2CH_2CH_3$ | $CH_2Br$ | H | H | H |
| Ia1.62 | $CH_3$ | $SO_2CH_2CH_3$ | $CH_2Br$ | $CH_3$ | H | H |
| Ia1.63 | $CH_3$ | $SO_2CH_2CH_3$ | $CHF_2$ | H | H | H |
| Ia1.64 | $CH_3$ | $SO_2CH_2CH_3$ | $CHF_2$ | $CH_3$ | H | H |
| Ia1.65 | $CH_3$ | $SO_2CH_2CH_3$ | $CHF_2$ | $CHF_2$ | H | H |
| Ia1.66 | $CH_3$ | $SO_2CH_2CH_3$ | $CF_3$ | H | H | H |
| Ia1.67 | $CH_3$ | $SO_2CH_2CH_3$ | $CF_3$ | $CF_3$ | H | H |
| Ia1.68 | $CH_3$ | $SO_2CH_2CH_3$ | $CF_3$ | $CH_3$ | H | H |
| Ia1.69 | $CH_3$ | $SO_2CH_2CH_3$ | $CHClCH_3$ | H | H | H |
| Ia1.70 | $CH_3$ | $SO_2CH_2CH_3$ | $CHBrCH_3$ | H | H | H |
| Ia1.71 | $CH_3$ | $SO_2CH_2CH_3$ | $CHFCH_3$ | H | H | H |
| Ia1.72 | $CH_3$ | $SO_2CH_2CH_3$ | $CF_2CF_3$ | H | H | H |

Extraordinary preference is also given to the compounds of the formula Ia2, in particular to the compounds Ia2.1 to Ia2.72 which differ from the corresponding compounds Ia1.1 to Ia1.72 only in that $R^{11}$ is methyl.

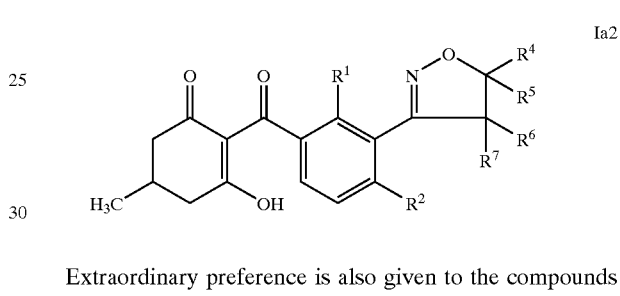

Extraordinary preference is also given to the compounds of the formula Ia3, in particular to the compounds Ia3.1 to Ia3.72 which differ from the compounds Ia1.1 to Ia1.72 only in that $R^{11}$ and $R^{12}$ are methyl.

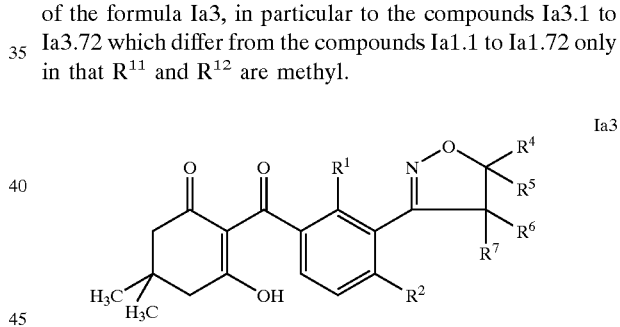

Extraordinary preference is also given to the compounds of the formula Ia4, in particular to the compounds Ia4.1 to Ia4.72 which differ from the compounds Ia1.1 to Ia1.72 only in that $R^9$ and $R^{13}$ are methyl.

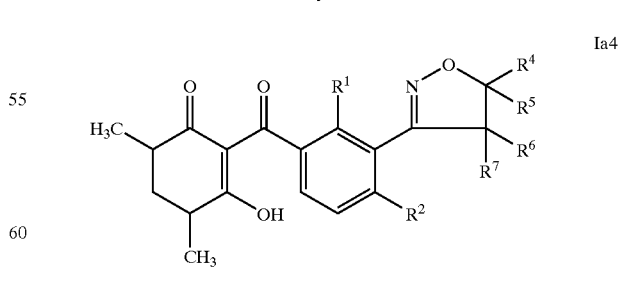

Extraordinary preference is also given to the compounds of the formula Ia5, in particular to the compounds Ia5.1 to Ia5.72 which differ from the compounds Ia1.1 to Ia1.72 only in that $R^9$ is methylthio and $R^{10}$ is methyl.

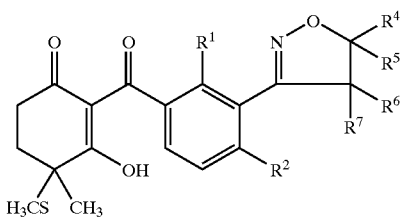

Ia5

Extraordinary preference is also given to the compounds of the formula Ia6, in particular to the compounds Ia6.1 to Ia6.72 which differ from the compounds Ia1.1 to Ia1.72 only in that $R^9$ and $R^{10}$ together are pentane-1,5-diyl.

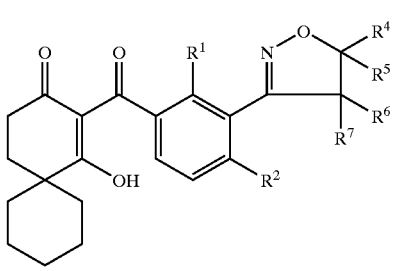

Ia6

Extraordinary preference is also given to the compounds of the formula Ia7, in particular to the compounds Ia7.1 to Ia7.72 which differ from the compounds Ia1.1 to Ia1.72 only in that $R^{10}$ and $R^{14}$ together are ethane-1,2-diyl.

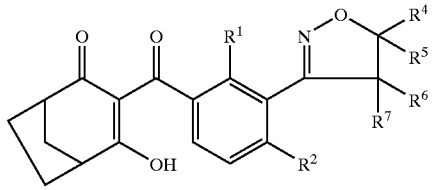

Ia7

Extraordinary preference is also given to the compounds of the formula Ia8, in particular to the compounds Ia8.1 to Ia8.72 which differ from the compounds Ia1.1 to Ia1.72 only in that $R^9$, $R^{10}$, $R^{13}$ and $R^{14}$ are methyl and $R^{11}$ and $R^{12}$ together are an oxygen atom.

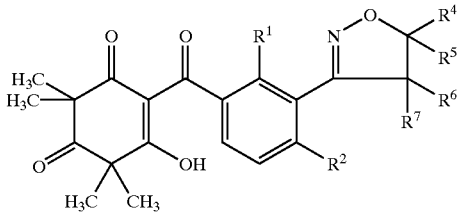

Ia8

Extraordinary preference is also given to the compounds of the formula Ia9, in particular to the compounds Ia9.1 to Ia9.72 which differ from the compounds Ia1.1 to Ia1.72 only in that $R^{11}$ is hydroxyl.

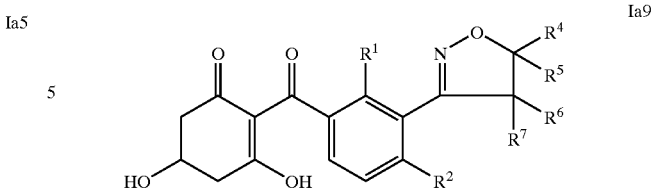

Ia9

The haloalkyl-substituted 3-(4,5-dihydroisoxazol-3-yl)benzoylcyclohexenones of the formula I can be obtained by different routes, for example by the processes below.

Process A:

Compounds of the formula I where $R^8=OH$ are obtained by reacting compounds of the formula II with an activated benzoic acid derivative IIIα or a benzoic acid IIIβ, which is preferably activated in situ, to give the corresponding acylation product I' and subsequent rearrangement.

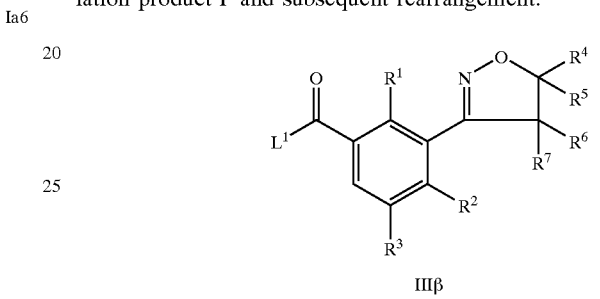

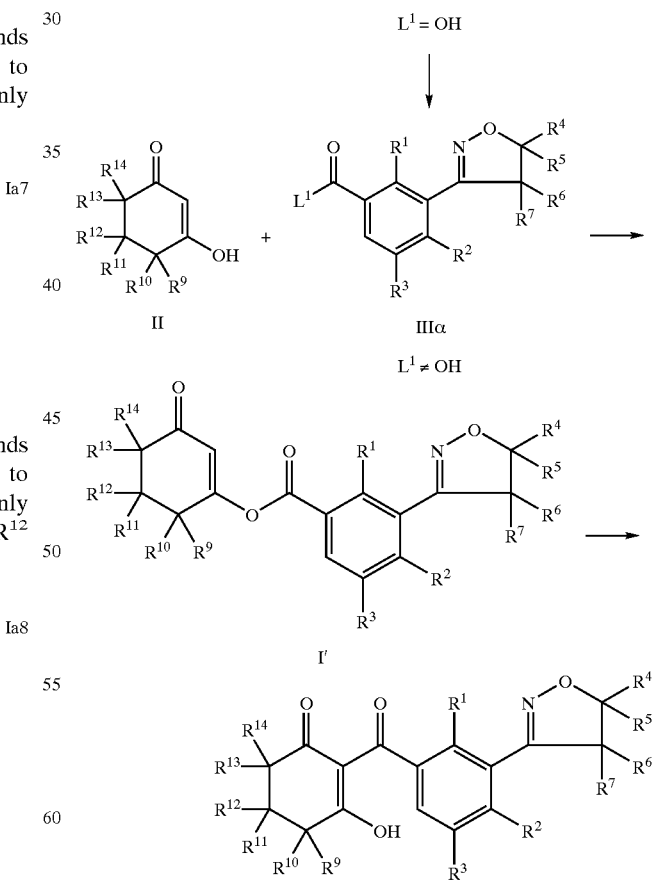

$L^1$ is hydroxyl or a nucleophilically displaceable leaving group, such as halogen, for example bromine or chlorine, hetaryl, for example imidazolyl or pyridyl, carboxylate, for example acetate, trifluoroacetate, etc.

The activated benzoic acid IIIα can be employed directly, such as in the case of the benzoyl halides, or be generated in situ, for example using dicyclohexylcarbodiimide, triphenylphosphine/azodicarboxylic ester, 2-pyridine disulfide/triphenylphosphine, carbonyldiimidazole, etc.

It may be advantageous to carry out the acylation reaction in the presence of a base. The reactants and the auxiliary base are in this case advantageously employed in equimolar amounts. A slight excess of auxiliary base, for example from 1.2 to 1.5 molar equivalents, based on II, may be advantageous in certain cases.

Suitable auxiliary bases are tertiary alkylamines, pyridine or alkali metal carbonates. Suitable for use as solvents are, for example, chlorinated hydrocarbons, such as methylene chloride, 1,2-dichloroethane, aromatic hydrocarbons, such as toluene, xylene, chlorobenzene, ethers, such as diethyl ether, methyl tert-butyl ether, dimethoxyethane, tetrahydrofuran, dioxane, polar aprotic solvents, such as acetonitrile, dimethylformamide, dimethyl sulfoxide, or esters, such as ethyl acetate or mixtures of these.

If the activated carboxylic acid component used is a benzoyl halide, it may be advantageous to cool the reaction mixture to 0–100° C. when adding this reaction partner. The mixture is subsequently stirred at 20–100° C., preferably at 25–50° C., until the reaction has ended. Work-up is carried out in a customary manner, for example by pouring the reaction mixture into water and extracting the product of value. Solvents which are particularly suitable for this purpose are methylene chloride, diethyl ether, dimethoxyethane and ethyl acetate. The organic phase is dried and the solvent is removed, after which the crude ester I' can be employed for the rearrangement without any further purification.

The rearrangement of the esters I' to the compounds of the formula I is advantageously carried out at 20–40° C. in a solvent and in the presence of a base and, if appropriate, using a cyano compound as catalyst.

Suitable solvents are, for example, acetonitrile, methylene chloride, 1,2-dichloroethane, dioxane, ethyl acetate, dimethoxyethane, tetrahydrofuran, toluene or mixtures of these. Preferred solvents are acetonitrile and dioxane.

Suitable bases are tertiary amines, such as triethylamine, pyridine or alkali metal carbonates, such as sodium carbonate or potassium carbonate, which are preferably employed in an equimolar amount or an up to four-fold excess, based on the ester. Preference is given to using triethylamine or alkali metal carbonates, preferably in twice the equimolar amount, based on the ester.

Suitable cyano compounds are inorganic cyanides, such as sodium cyanide and potassium cyanide, and organic cyano compounds, such as acetone cyanohydrin and trimethylsilyl cyanide. They are employed in an amount of from 1 to 50 mol percent, based on the ester. Preference is given to using acetone cyanohydrin or trimethylsilyl cyanide, for example in an amount of from 5 to 15, preferably 10, mol percent, based on the ester (examples of cyanide-catalyzed rearrangements of enol esters of cyclohexane-1,3-diones are mentioned, for example, in EP-A 186 118 and U.S. Pat. No. 4,780,127).

Work-up can be carried out in a manner known per se. The reaction mixture is, for example, acidified with dilute mineral acid, such as 5% strength hydrochloric acid or sulfuric acid, and extracted with an organic solvent, for example methylene chloride or ethyl acetate. The organic extract can be extracted with 5–10% strength alkali metal carbonate solution, for example sodium carbonate or potassium carbonate solution. The aqueous phase is acidified and the resulting precipitate is filtered off with suction and/or extracted with methylene chloride or ethyl acetate, and the mixture is dried and concentrated.

The cyclohexenones of the formula II are known or can be prepared by processes known per se (for example EP-A 71 707, EP-A 142 741, EP-A 243 313, U.S. Pat. No. 4,249,937, WO 92/13821).

The compounds of the formula IIIβ can be obtained, for example, as follows:

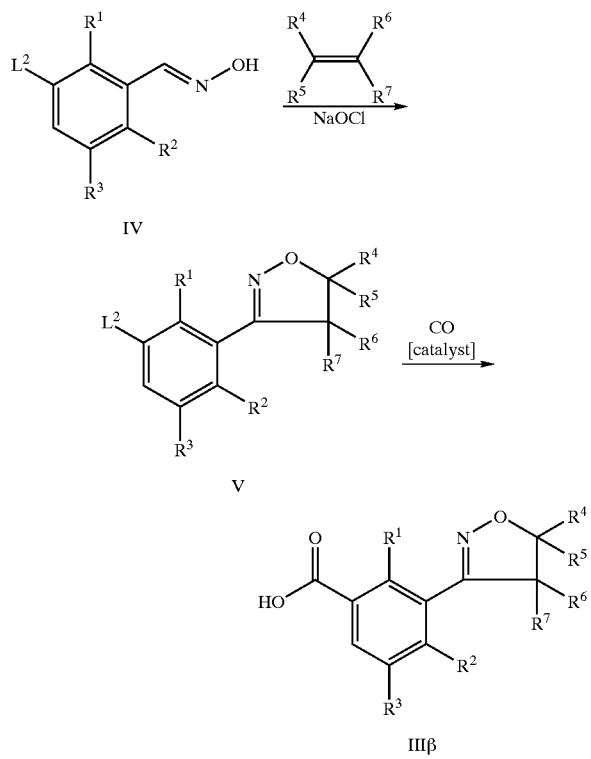

$L^2$ is a leaving group, such as halogen, for example chlorine, bromine or iodine, or sulfonate, such as mesylate or triflate; preference is given to bromine or triflate.

The 4,5-dihydroisoxazol-3-ylbenzene derivatives V can be obtained, for example, by converting oximes of the formula IV in a manner known per se via the hydroxamic acid chloride intermediates. The latter are used to generate, in situ, nitrile oxides which react with alkenes to form the desired products (cf., for example, Chem. Ber. 106 (1972), 3258–3274).

The 4,5-dihydroisoxazol-3-ylbenzene derivative V is then reacted with carbon monoxide and water in the presence of a catalyst and of a base to give IIIβ.

Suitable catalysts are palladium-ligand complexes in which the palladium is present in oxidation state 0, metallic palladium, which has optionally been absorbed on a support, and preferably palladium(II) salts. The reaction with palladium(II) salts and metallic palladium is preferably carried out in the presence of complex ligands.

An example of a suitable palladium(0)-ligand complex is tetrakis(triphenylphosphine)palladium.

Metallic palladium is preferably absorbed on an inert support such as, for example, activated carbon, silica, alumina, barium sulfate or calcium carbonate. The reaction is preferably carried out in the presence of complex ligands such as, for example, triphenylphosphine.

Examples of suitable palladium(II) salts are palladium acetate and palladium chloride. The presence of complex ligands such as, for example, triphenylphosphine is preferred.

Suitable complex ligands for the palladium-ligand complexes, or in whose presence the reaction with metallic palladium or palladium(II) salts is preferably carried out, are tertiary phosphines whose structure is represented by the following formulae:

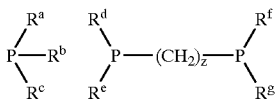

where z is 1 to 4 and the radicals $R^a$ to $R^g$ are $C_1$–$C_6$-alkyl, $C_3$–$C_6$-cycloalkyl, aryl-$C_1$–$C_2$–alkyl or, preferably, aryl. Aryl is, for example, naphthyl and unsubstituted or substituted phenyl such as, for example, 2-tolyl and, in particular, unsubstituted phenyl.

The complex palladium salts can be prepared in a manner known per se starting from commercially available palladium salts such as palladium chloride or palladium acetate and the appropriate phosphines, such as, for example, triphenylphosphine or 1,2-bis(diphenylphosphino)ethane. Many of the complexed palladium salts are also commercially available. Preferred palladium salts are [(R)(+)-2,2'-bis (diphenylphosphino)-1,1'-binaphthyl]-palladium(II) chloride, bis(triphenylphosphine)palladium(II) acetate and, in particular, bis(triphenylphosphine)palladium(II) chloride.

The palladium catalyst is usually employed in a concentration of from 0.05 to 5 mol %, and preferably 1 to 3 mol %.

Suitable bases are tertiary amines, such as, for example, N-methylpiperidine, ethyldiisopropylamine, 1,8-bisdimethylaminonaphthalene or, in particular, triethylamine. Also suitable is alkali metal carbonate, such as sodium carbonate or potassium carbonate. However, mixtures of potassium carbonate and triethylamine are also suitable.

In general, from 2 to 4 molar equivalents, in particular 2 molar equivalents, of the alkali metal carbonate, and from 1 to 4 molar equivalents, in particular 2 molar equivalents, of the tertiary amine are employed, based on the 4,5-dihydroisoxazol-3-ylbenzene derivative of the formula V.

Suitable solvents are nitriles, such as benzonitrile and acetonitrile, aromatic hydrocarbons, such as toluene, amides, such as dimethylformamide, dimethylacetamide, tetra-$C_1$–$C_4$-alkylureas or N-methylpyrrolidone and, preferably, ethers, such as tetrahydrofuran and methyl tert-butyl ether. Particular preference is given to ethers, such as 1,4-dioxane and dimethoxyethane.

It is also possible to obtain the compounds of the formula IIIα ($L^1$=OH) by converting an oxime of the formula VI into the corresponding hydroxamic acid halide, in particular hydroxamic acid chloride, generating, in situ, a nitrile oxide and reacting this with an alkene (cf., for example, Chem. Ber. 106 (1973), 3258–3274). The ester VII is then hydrolyzed under conditions known per se to give the compounds of the formula III where $L^1$=hydroxyl.

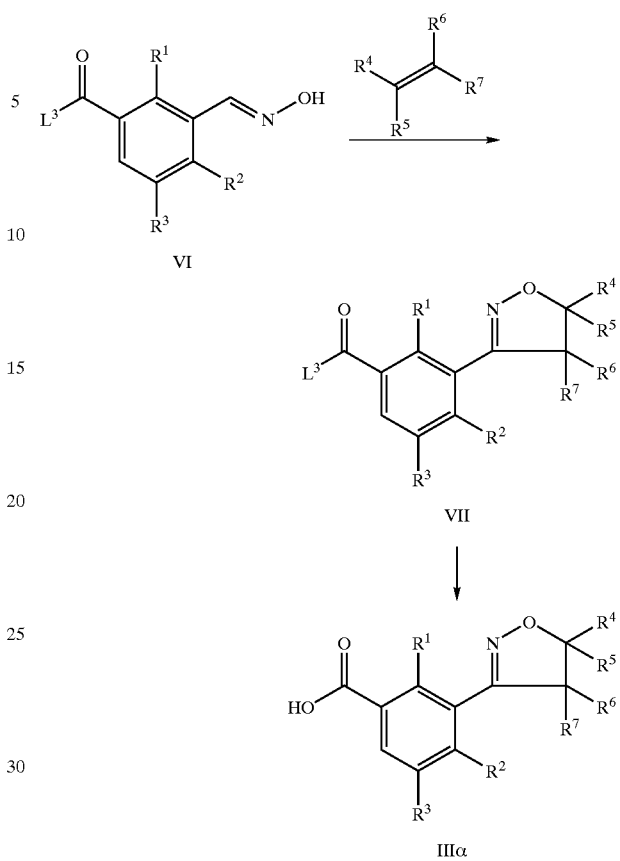

$L^3$ is a $C_1$–$C_6$-alkoxy radical.

Compounds of the formula I where $R^8$=$OR^{15}$ and $SR^{15}$ are obtained by reacting compounds of the formula I where $R^8$=hydroxyl and mercapto, respectively, with alkylating agents, carbamoylating agents or acylating agents $L^4$–$R^{15}$ (IV).

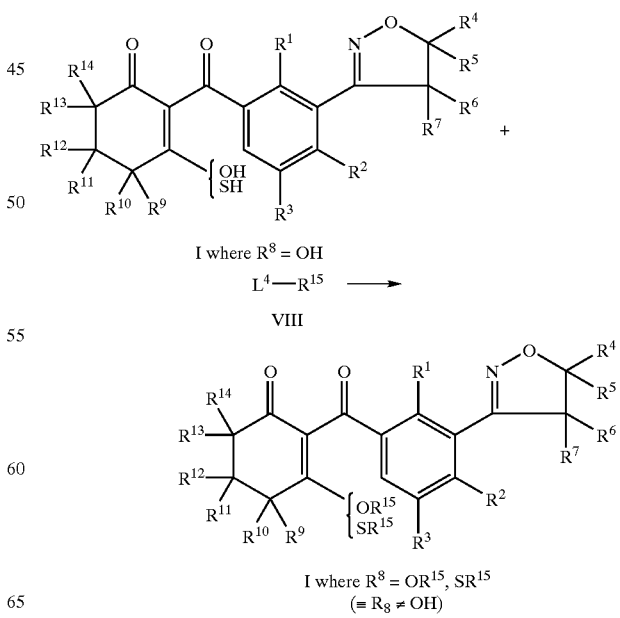

$L^4$ is a nucleophilically displaceable leaving group, such as halogen, for example bromine or chlorine, acyloxy, for example acetyloxy or ethylcarbonyloxy, or alkylsulfonyloxy, for example methylsulfonyloxy or trifluoromethylsulfonyloxy.

The compounds of the formula VIII can be employed directly, such as, for example, in the case of the carbonyl halides or carboxylic anhydrides, or be generated in situ (for example using dicyclohexylcarbodiimide, carbonyldiimidazole etc.).

The starting materials are generally employed in equimolar amounts. However, it may also be advantageous to employ an excess of one or the other component.

If appropriate, it may be advantageous to carry out the reaction in the presence of a base. The reactants and the auxiliary base are advantageously employed in equimolar amounts. An excess of auxiliary base, for example from 1.5 to 3 molar equivalents, based on I, may be advantageous in certain cases.

Suitable auxiliary bases are tertiary alkylamines, such as triethylamine, aromatic amines, such as pyridine, alkali metal carbonates, for example sodium carbonate or potassium carbonate, alkali metal bicarbonates, such as sodium bicarbonate or potassium bicarbonate, alkali metal alkoxides, such as sodium methoxide, sodium ethoxide or potassium tert-butoxide, or alkali metal hydrides, for example sodium hydride. Preference is given to using triethylamine and pyridine.

Suitable solvents are, for example, chlorinated hydrocarbons, such as methylene chloride and 1,2-dichloroethane, aromatic hydrocarbons, for example toluene, xylene, chlorobenzene, ethers, such as diethyl ether, methyl tert-butyl ether, tetrahydrofuran and dioxane, polar aprotic solvents, such as acetonitrile and dimethylformamide, dimethyl sulfoxide, or esters, such as ethyl acetate, or mixtures of these.

In general, the reaction temperature is in the range from 0° C. to the boiling point of the reaction mixture.

Work-up can be carried out in a manner known per se to give the product.

Compounds of the formula I where $R^8$=halogen are obtained by reacting compounds of the formula I where $R^8$=hydroxyl with a halogenating agent (Hal denotes halogen).

Suitable halogenating agents are, for example, phosgene, diphosgene, triphosgene, thionyl chloride, oxalyl chloride, phosphorus oxychloride, phosphorus pentachloride, mesyl chloride, chloromethylene-N,N-dimethylammonium chloride, oxalyl bromide, phosphorus oxybromide, etc.

The starting materials are generally employed in equimolar amounts. It may also be advantageous to employ an excess of one or the other component.

Suitable solvents are, for example, chlorinated hydrocarbons, such as methylene chloride or 1,2-dichloroethane, aromatic hydrocarbons, for example toluene, xylene or chlorobenzene, polar aprotic solvents, such as acetonitrile, dimethylformamide or dimethyl sulfoxide, or mixtures of these. It is also possible to carry out the reaction without using a solvent.

In general, the reaction temperature is in the range from 0° C. to the boiling point of the reaction mixture.

Work-up can be carried out in a manner known per se to give the product.

Compounds of the formula I where $R^8$=mercapto, $OR^{15}$ or $SR^{15}$ can be obtained by reacting compounds of the formula I where $R^8$=halogen with compounds IX, if appropriate in the presence of a base or with prior salt formation.

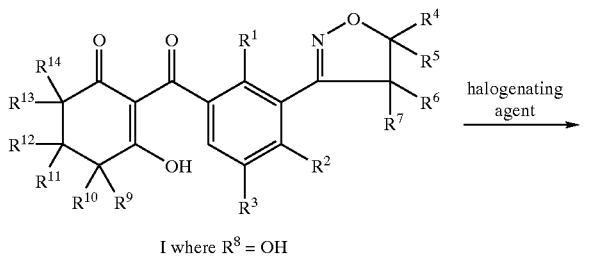

The starting materials are generally employed in equimolar amounts. However, it may also be advantageous to employ an excess of one or the other component.

If appropriate, it may also be advantageous to carry out the reaction in the presence of a base. The reactants and the base are advantageously employed in equimolar amounts. An excess of base, for example from 1.5 to 3 molar equivalents, based on I where $R^8$=Hal, may be advantageous in certain cases.

Suitable bases are tertiary alkylamines, such as triethylamine, aromatic amines, such as pyridine, alkali metal carbonates, for example sodium carbonate or potassium carbonate, alkali metal bicarbonates, such as sodium bicarbonate or potassium bicarbonate, alkali metal alkoxides, such as sodium methoxide, sodium ethoxide or potassium tert-butoxide or alkali metal hydrides, such as, for example, sodium hydride. Preference is given to using sodium hydride or potassium tert-butoxide.

Suitable solvents are, for example, chlorinated hydrocarbons, such as methylene chloride and 1,2-dichloroethane, aromatic hydrocarbons, for example toluene, xylene or chlorobenzene, ethers, such as diethyl ether, methyl tert-butyl ether, tetrahydrofuran or dioxane, polar aprotic solvents, such as acetonitrile, dimethylformamide or dimethyl sulfoxide, or mixtures of these.

In general, the reaction temperature is in the range from 0° C. to the boiling point of the reaction mixture.

Work-up can be carried out in a manner known per se to give the product.

It is furthermore possible to obtain compounds of the formula I where $R^8=SOR^{16}$ or $SO_2R^{16}$ using an oxidizing agent.

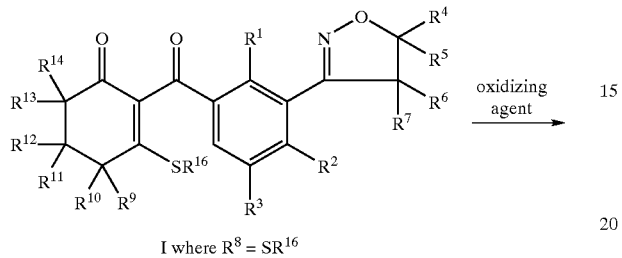

I where $R^8 = SR^{16}$

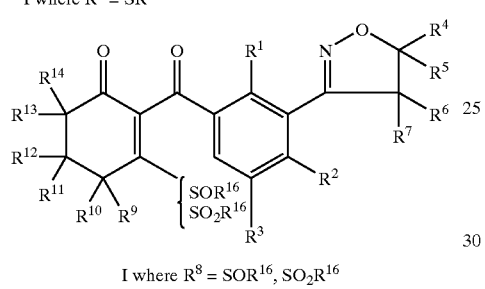

I where $R^8 = SOR^{16}, SO_2R^{16}$

Suitable oxidizing agents are, for example, m-chloroperbenzoic acid, peroxyacetic acid, trifluoroperoxyacetic acid, hydrogen peroxide, if appropriate in the presence of a catalyst, such as tungstate.

The starting materials are generally employed in equimolar amounts. It may be advantageous to employ an excess of one or the other component.

Suitable solvents are, for example, chlorinated hydrocarbons, such as methylene chloride or 1,2-dichloroethane, aromatic hydrocarbons, for example toluene, xylene or chlorobenzene, ethers, such as diethyl ether, methyl tert-butyl ether, tetrahydrofuran or dioxane, polar aprotic solvents, such as acetonitrile or dimethylformamide, or esters, such as ethyl acetate, or mixtures of these.

In general, the reaction temperature is in the range from 0° C. to the boiling point of the reaction mixture.

Work-up can be carried out in a manner known per se to give the product.

PREPARATION EXAMPLES

2-Methyl-3-(5-chloromethyl-4,5-dihydroisoxazol-3-yl)-4-methyl-sulfonylbenzoyl Chloride 3.23 g (27.2 mmol) of thionyl chloride were added dropwise to a mixture of 4.5 g (13.6 mmol) of 2-methyl-3-(5-chloromethyl-4,5-dihydroisoxazol-3-yl)-4-methyl-sulfonylbenzoic acid, 100 ml of toluene and three drops of N,N-dimethylformamide. The mixture was refluxed for 4 hours and then cooled, and the solvent was removed. The residue was then taken up in methylene chloride and once more concentrated to dryness. This gave 4.74 g (100% of theory) of the title compound in the form of a pale powder.

3-[2-Methyl-3-(5-chloromethyl-4,5-dihydroisoxazol-3-yl)-4-methyl-sulfonylbenzoyl]bicyclo[3.2.1]octane-2,4-dione (Compound 2.2)

Under nitrogen and at 0–5° C., 0.7 g (2 mmol) of 2-methyl-3-(5-chloromethyl-4,5-dihydroisoxazol-3-yl)-4-methyl-sulfonylbenzoyl chloride in 40 ml of acetonitrile was added dropwise to 0.28 g (2 mmol) of bicyclo[3.2.1]octane-2,4-dione and 0.4 g (4 mmol) of triethylamine in 40 ml of acetonitrile, and the mixture was stirred at room temperature for 4 hours. 1 drop of trimethylsilyl cyanide and 0.05 g of potassium carbonate were then added, and the mixture was stirred at 40° C. for 2 hours and then at room temperature for 12 hours. Following this, the solvent was removed, the residue was taken up in ethyl acetate and the solution was extracted repeatedly with 5% strength potassium carbonate solution. The combined extracts were then adjusted to pH 2–3 using 10% strength hydrochloric acid and extracted repeatedly with methylene chloride. These combined organic extracts were then washed with water and dried, and the solvent was removed. The oily yellow residue was chromatographed over silica gel (mobile phase: methylene chloride/methanol=99/1 to 97/3). This gave 0.4 g (44% of theory) of the title compound of melting point 98–103° C.

Table 2 lists compounds of the formula I which were prepared or are preparable in a similar manner.

TABLE 2

I

| No. | $R^1$ | $R^2$ | $R^3$ | $R^4$ | $R^5$ | $R^6$ | $R^7$ | $R^8$ | $R^9$ | $R^{10}$ | $R^{11}$ | $R^{12}$ | $R^{13}$ | $R^{14}$ | Physical data m.p. [° C.] |
|---|---|---|---|---|---|---|---|---|---|---|---|---|---|---|---|
| 2.1 | $CH_3$ | $CH_3SO_2$ | H | $CH_2Cl$ | H | H | H | OH | H | H | $CH_3$ | $CH_3$ | H | H | 93–94 |
| 2.2 | $CH_3$ | $CH_3SO_2$ | H | $CH_2Cl$ | H | H | H | OH | H | 1) | H | H | H | 1) | 98–103 |
| 2.3 | $CH_3$ | $CH_3SO_2$ | H | $CH_2Cl$ | H | H | H | OH | $CH_3$ | $CH_3$ | | =O | $CH_3$ | $CH_3$ | 143–153 |
| 2.4 | $CH_3$ | $CH_3SO_2$ | H | $CH_2Cl$ | H | H | H | OH | $CH_3$ | H | H | H | $CH_3$ | H | 119–123 |

TABLE 2-continued

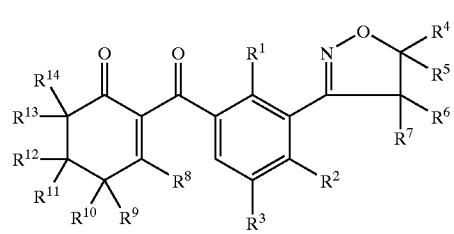

| No. | R$^1$ | R$^2$ | R$^3$ | R$^4$ | R$^5$ | R$^6$ | R$^7$ | R$^8$ | R$^9$ | R$^{10}$ | R$^{11}$ | R$^{12}$ | R$^{13}$ | R$^{14}$ | Physical data m.p. [° C.] |
|---|---|---|---|---|---|---|---|---|---|---|---|---|---|---|---|
| 2.5 | CH$_3$ | CH$_3$SO$_2$ | H | CH$_2$Cl | H | H | H | OH | SCH$_3$ | CH$_3$ | H | H | H | H | 83–87 |
| 2.6 | CH$_3$ | CH$_3$SO$_2$ | H | CH$_2$Cl | H | H | H | OH | —(CH$_2$)$_5$— | | H | H | H | H | 75–81 |
| 2.7 | CH$_3$ | CH$_3$SO$_2$ | H | CH$_2$Cl | CH$_2$Cl | H | H | OH | H | H | CH$_3$ | CH$_3$ | H | H | 94–99 |
| 2.8 | CH$_3$ | CH$_3$SO$_2$ | H | CH$_2$Cl | CH$_2$Cl | H | H | OH | —(CH$_2$)$_5$— | | H | H | H | H | 66–70 |
| 2.9 | CH$_3$ | CH$_3$SO$_2$ | H | CH$_2$Cl | CH$_2$Cl | H | H | OH | H | 1) | H | H | H | 1) | 81–85 |
| 2.10 | CH$_3$ | CH$_3$SO$_2$ | H | CH$_2$Cl | CH$_2$Cl | H | H | OH | CH$_3$ | H | H | H | CH$_3$ | H | 84–91 |
| 2.11 | CH$_3$ | CH$_3$SO$_2$ | H | CH$_2$Cl | CH$_2$Cl | H | H | OH | CH$_3$ | CH$_3$ | =O | | CH$_3$ | CH$_3$ | 131–140 |
| 2.12 | CH$_3$ | CH$_3$SO$_2$ | H | CH$_2$Cl | CH$_2$Cl | H | H | OH | SCH$_3$ | CH$_3$ | H | H | H | H | 70–75 |
| 2.13 | CH$_3$ | CH$_3$SO$_2$ | H | CH$_2$Cl | CH$_3$ | H | H | OH | H | H | CH$_3$ | CH$_3$ | H | H | 91–94 |
| 2.14 | CH$_3$ | CH$_3$SO$_2$ | H | CH$_2$F | H | H | H | OH | H | H | CH$_3$ | CH$_3$ | H | H | 84–87 |
| 2.15 | CH$_3$ | CH$_3$SO$_2$ | H | CH$_2$F | H | H | H | OH | H | 1) | H | H | H | 1) | 121–129 |
| 2.16 | CH$_3$ | CH$_3$SO$_2$ | H | CH$_2$F | H | H | H | OH | CH$_3$ | CH$_3$ | =O | | CH$_3$ | CH$_3$ | 80–85 |
| 2.17 | CH$_3$ | CH$_3$SO$_2$ | H | CH$_2$F | H | H | H | OH | CH$_3$ | H | H | H | CH$_3$ | H | 73–76 |
| 2.18 | CH$_3$ | CH$_3$SO$_2$ | H | CH$_2$Cl | CH$_3$ | H | H | OH | H | 1) | H | H | H | 1) | 118–123 |
| 2.19 | CH$_3$ | CH$_3$SO$_2$ | H | CH$_2$Cl | CH$_3$ | H | H | OH | CH$_3$ | H | H | H | CH$_3$ | H | 112–117 |
| 2.20 | CH$_3$ | CH$_3$SO$_2$ | H | CH$_2$Cl | CH$_3$ | H | H | OH | CH$_3$ | CH$_3$ | =O | | CH$_3$ | CH$_3$ | 88–93 |
| 2.21 | CH$_3$ | CH$_3$SO$_2$ | H | CH$_2$Cl | CH$_3$ | H | H | OH | CH$_3$ | CH$_3$ | H | H | H | H | 80–85 |
| 2.22$^{2)}$ | CH$_3$ | CH$_3$SO$_2$ | H | CH$_2$Cl | H | CH$_3$ | H | OH | H | 1) | H | H | H | 1) | 89–96 |
| 2.23$^{2)}$ | CH$_3$ | CH$_3$SO$_2$ | H | CH$_2$Cl | H | CH$_3$ | H | OH | H | H | CH$_3$ | CH$_3$ | H | H | 109–116 |
| 2.24$^{3)}$ | CH$_3$ | CH$_3$SO$_2$ | H | CH$_2$Cl | H | CH$_3$ | H | OH | H | 1) | H | H | H | 1) | 92–96 |
| 2.25$^{3)}$ | CH$_3$ | CH$_3$SO$_2$ | H | CH$_2$Cl | H | CH$_3$ | H | OH | H | H | CH$_3$ | CH$_3$ | H | H | 97–103 |
| 2.26 | CH$_3$ | CH$_3$SO$_2$ | H | CHF$_2$ | H | H | H | OH | H | H | CH$_3$ | CH$_3$ | H | H | 146–150 |
| 2.27 | CH$_3$ | CH$_3$SO$_2$ | H | CHF$_2$ | H | H | H | OH | H | 1) | H | H | H | 1) | 134–140 |
| 2.28 | CH$_3$ | CH$_3$SO$_2$ | H | CHF$_2$ | H | H | H | OH | CH$_3$ | CH$_3$ | =O | | CH$_3$ | CH$_3$ | 86–91 |
| 2.29 | CH$_3$ | CH$_3$SO$_2$ | H | CHF$_2$ | H | H | H | OH | CH$_3$ | CH$_3$ | H | H | H | H | 79–83 |
| 2.30 | CH$_3$ | CH$_3$SO$_2$ | H | CHF$_2$ | H | H | H | OH | CH$_3$ | H | H | H | CH$_3$ | H | 73–78 |
| 2.31 | CH$_3$ | CH$_3$SO$_2$ | H | CHF$_2$ | H | H | H | OH | H | H | H | H | H | H | 169–174 |
| 2.32 | CH$_3$ | CH$_3$SO$_2$ | H | CHF$_2$ | H | H | H | OH | H | H | H | H | H | H | 76–80 |

1) R$^{10}$ and R$^{14}$ together = —CH$_2$CH$_2$—
2) R$^4$/R$^6$ are trans to one another
3) R$^4$/R$^6$ are cis to one another The haloalkyl-substituted 3-(4,5-dihydroisoxazol-3-yl) benzoylcyclohexenones of the formula I and their agriculturally useful salts are suitable, both in the form of isomer mixtures and in the form of the pure isomers, as herbicides. The herbicidal compositions comprising compounds of the formula I control vegetation on non-crop areas very efficiently, especially at high rates of application. They act against broad-leaved weeds and harmful grasses in crops such as wheat, rice, maize, soya and cotton without causing any significant damage to the crop plants. This effect is mainly observed at low rates of application.

Depending on the application method used, the compounds of the formula I or the herbicidal compositions comprising them, can additionally be employed in a further number of crop plants for eliminating undesirable plants. Examples of suitable crops are the following:

*Allium cepa, Ananas comosus, Arachis hypogaea, Asparagus officinalis, Beta vulgaris* spec. *altissima, Beta vulgaris* spec. *rapa, Brassica napus* var. *napus, Brassica napus* var. *napobrassica, Brassica rapa* var. *silvestris, Camellia sinensis, Carthamus tinctorius, Carya illinoinensis, Citrus limon, Citrus sinensis, Coffea arabica* (*Coffea canephora, Coffea liberica*), *Cucumis sativus, Cynodon dactylon, Daucus carota, Elaeis guineensis, Fragaria vesca, Glycine max, Gossypium hirsutum,* (*Gossypium arboreum, Gossypium herbaceum, Gossypium vitifolium*), *Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus* spec., *Manihot esculenta, Medicago sativa, Musa* spec., *Nicotiana tabacum* (*N.rustica*), *Olea europaea, Oryza sativa, Phaseolus lunatus, Phaseolus vulgaris, Picea abies, Pinus* spec., *Pisum sativum, Prunus avium, Prunus persica, Pyrus communis, Ribes sylvestre, Ricinus communis, Saccharum officinarum, Secale cereale, Solanum tuberosum, Sorghum bicolor* (*s. vulgare*), *Theobroma cacao, Trifolium pratense, Triticum aestivum, Triticum durum, Vicia faba, Vitis vinifera* and *Zea mays*.

In addition, the compounds of the formula I may also be used in crops which tolerate the action of herbicides owing to breeding, including genetic engineering methods.

The compounds of the formula I, or the herbicidal compositions comprising them, can be used for example in the form of ready-to-spray aqueous solutions, powders, suspensions, also highly-concentrated aqueous, oily or other suspensions or dispersions, emulsions, oil dispersions, pastes, dusts, materials for broadcasting or granules, by means of spraying, atomizing, dusting, broadcasting or watering. The use forms depend on the intended aims; in any case, they should ensure a very fine distribution of the active compounds according to the invention.

The herbicidal compositions comprise a herbicidally effective amount of at least one compound of the formula I or an agriculturally useful salt of I and auxiliaries customarily used for formulating crop protection agents.

Essentially, suitable inert auxiliaries include: mineral oil fractions of medium to high boiling point, such as kerosene and diesel oil, furthermore coal tar oils and oils of vegetable or animal origin, aliphatic, cyclic and aromatic hydrocarbons, e.g. paraffins, tetrahydronaphthalene, alkylated naphthalenes and their derivatives, alkylated benzenes and their derivatives, alcohols such as methanol, ethanol, propanol, butanol and cyclohexanol, ketones such as cyclohexanone, strongly polar solvents, e.g. amines such as N-methylpyrrolidone and water.

Aqueous use forms can be prepared from emulsion concentrates, suspensions, pastes, wettable powders or water-dispersible granules by adding water. To prepare emulsions, pastes or oil dispersions, the haloalkyl-substituted 3-(4,5-dihydroisoxazol-3-yl)benzoylcyclohexenones, either as such or dissolved in an oil or solvent, can be homogenized in water by means of a wetting agent, tackifier, dispersant or emulsifier. Alternatively, it is possible to prepare concentrates consisting of active substance, wetting agent, tackifier, dispersant or emulsifier and, if desired, solvent or oil, which are suitable for dilution with water.

Suitable surfactants (adjuvants) are the alkali metal salts, alkaline earth metal salts and ammonium salts of aromatic sulfonic acids, e.g. ligno-, phenol-, naphthalene- and dibutylnaphthalenesulfonic acid, and of fatty acids, alkyl- and alkylarylsulfonates, alkyl sulfates, lauryl ether sulfates and fatty alcohol sulfates, and salts of sulfated hexa-, hepta- and octadecanols, and also of fatty alcohol glycol ethers, condensates of sulfonated naphthalene and its derivatives with formaldehyde, condensates of naphthalene, or of the naphthalenesulfonic acids with phenol and formaldehyde, polyoxyethylene octylphenol ether, ethoxylated isooctyl-, octyl- or nonylphenol, alkylphenyl or tributylphenyl polyglycol ether, alkylaryl polyether alcohols, isotridecyl alcohol, fatty alcohol ethylene oxide condensates, ethoxylated castor oil, polyoxyethylene alkyl ethers or polyoxypropylene alkyl ethers, lauryl alcohol polyglycol ether acetate, sorbitol esters, lignosulfite waste liquors or methylcellulose.

Powders, materials for broadcasting and dusts can be prepared by ixing or grinding the active substances together with a solid carrier.

Granules, e.g. coated granules, impregnated granules and homogeneous granules, can be prepared by binding the active compounds to solid carriers. Solid carriers are mineral earths, such as silicas, silica gels, silicates, talc, kaolin, limestone, lime, chalk, bole, loess, clay, dolomite, diatomaceous earth, calcium sulfate, magnesium sulfate, magnesium oxide, ground synthetic materials, fertilizers such as ammonium sulfate, ammonium phosphate, ammonium nitrate and ureas, and products of vegetable origin, such as cereal meal, tree bark meal, wood meal and nutshell meal, cellulose powders, or other solid carriers.

The concentrations of the compounds of the formula I in the ready-to-use preparations can be varied within wide ranges. In general, the formulations comprise from about 0.001 to 98% by weight, preferably 0.01 to 95% by weight of at least one active compound. The active compounds are employed in a purity of from 90% to 100%, preferably from 95% to 100% (according to the NMR spectrum).

The production of such preparations is illustrated by the following formulation examples:

I 20 parts by weight of the compound No. 2.1 are dissolved in a mixture consisting of 80 parts by weight of alkylated benzene, 10 parts by weight of the adduct of 8 to 10 mol of ethylene oxide to 1 mol of oleic acid N-monoethanolamide, 5 parts by weight of calcium dodecylbenzenesulfonate and 5 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active compound.

II 20 parts by weight of the compound No. 2.1 are dissolved in a mixture consisting of 40 parts by weight of cyclohexanone, 30 parts by weight of isobutanol, 20 parts by weight of the adduct of 7 mol of ethylene oxide to 1 mol of isooctylphenol and 10 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active compound.

III 20 parts by weight of the active compound No. 2.1 are dissolved in a mixture consisting of 25 parts by weight of cyclohexanone, 65 parts by weight of a mineral oil fraction of boiling point 210 to 280° C. and 10 parts by weight of an adduct of 40 mol of ethylene oxide to 1 mol of castor oil. Pouring the solution into 100,000 parts by weight of water and finely distributing it therein gives an aqueous dispersion which comprises 0.02% by weight of the active compound.

IV 20 parts by weight of the active compound No. 2.1 are mixed thoroughly with 3 parts by weight of sodium diisobutylnaphthalenesulfonate, 17 parts by weight of the sodium salt of lignosulfonic acid from a sulfite waste liquor and 60 parts by weight of pulverulent silica gel, and the mixture is ground in a hammer mill. Finely distributing the mixture in 20,000 parts by weight of water gives a spray mixture which comprises 0.1% by weight of the active compound.

V 3 parts by weight of the active compound No. 2.1 are mixed with 97 parts by weight of finely divided kaolin. This gives a dust which comprises 3% by weight of the active compound.

VI 20 parts by weight of the active compound No. 2.1 are mixed intimately with 2 parts by weight of the calcium salt of dodecylbenzenesulfonate, 8 parts by weight of fatty alcohol polyglycol ether, 2 parts by weight of the sodium salt of a phenol/urea/formaldehyde condensate and 68 parts by weight of a paraffinic mineral oil. This gives a stable oily dispersion.

VII 1 part by weight of the active compound No. 2.1 is dissolved in a mixture consisting of 70 parts by weight of cyclohexanone, 20 parts by weight of ethoxylated isooctylphenol and 10 parts by weight of ethoxylated castor oil. This gives a stable emulsion concentrate.

VIII. 1 part by weight of the active compound No. 2.1 is dissolved in a mixture of 80 parts by weight of cyclohexanone and 20 parts by weight of Wettol® EM 31 (=nonionic emulsifier based on ethoxylated castor oil). This gives a stable emulsion concentrate.

The compounds of the formula I or the herbicidal compositions can be applied pre- or post-emergence. If the active compounds are less well tolerated by certain crop plants, application techniques may be used in which the herbicidal compositions are sprayed, with the aid of the spraying equipment, in such a way that they come into contact as little as possible, if at all, with the leaves of the sensitive crop plants, while the active compounds reach the leaves of undesirable plants growing underneath, or the bare soil surface (post-directed, lay-by).

The application rates of the compound of the formula I are from 0.001 to 3.0, preferably from 0.01 to 1.0 kg/ha of active substance (a.s.), depending on the control target, the season, the target plants and the growth stage.

To widen the activity spectrum and to achieve synergistic effects, the haloalkyl-substituted 3-(4,5-dihydroisoxazol-3-yl)benzoylcyclohexenones of the formula I may be mixed with a large number of representatives of other herbicidal or growth-regulating active compound groups and then applied concomitantly. Suitable components for mixtures are, for example, 1,2,4-thiadiazoles, 1,3,4-thiadiazoles, amides, aminophosphoric acid and its derivatives, aminotriazoles, anilides, (het)aryloxyalkanoic acids and their derivatives, benzoic acid and its derivatives, benzothiadiazinones, 2-(hetaroyl/aroyl)-1,3-cyclohexandiones, hetaryl-aryl ketones, benzylisoxazolidinones, meta-CF$_3$-phenyl derivatives, carbamates, quinolinecarboxylic acid and its derivatives, chloroacetanilides, cyclohexenone oxime ether derivatives, diazines, dichloropropionic acid and its derivatives, dihydrobenzofurans, dihydrofuran-3-ones, dinitroanilines, dinitrophenols, diphenyl ether, dipyridyls, halocarboxylic acids and their derivatives, ureas, 3-phenyluracils, imidazoles, imidazolinones, N-phenyl-3,4, 5,6-tetrahydrophthalimides, oxadiazoles, oxiranes, phenols, aryloxy- and hetaryloxyphenoxypropionic esters, phenylacetic acid and their derivatives, 2-phenylpropionic acid and its derivatives, pyrazoles, phenylpyrazoles, pyridazines, pyridinecarboxylic acid and its derivatives, pyrimidyl ethers, sulfonamides, sulfonylureas, triazines, triazinones, triazolinones, triazolecarboxamides and uracils.

It may furthermore be advantageous to apply the compounds of the formula I, alone or else concomitantly in combination with other herbicides, or in the form of a mixture with other crop protection agents, for example together with agents for controlling pests or phytopathogenic fungi or bacteria. Also of interest is the miscibility with mineral salt solutions, which are employed for treating nutritional and trace element deficiencies. Non-phytotoxic oils and oil concentrates may also be added.

USE EXAMPLES

The herbicidal activity of the haloalkyl-substituted 3-(4, 5-dihydroisoxazol-3-yl)benzoylcyclohexenones of the formula I was demonstrated by the following greenhouse experiments:

The cultivation containers used were plastic pots containing loamy sand with approximately 3.0% of humus as the substrate. The seeds of the test plants were sown separately for each species.

For the pre-emergence treatment, directly after sewing the active compounds, which had been suspended or emulsified in water, were applied by means of finely distributing nozzles. The containers were irrigated gently to promote germination and growth and subsequently covered with transparent plastic hoods until the plants had rooted. This cover caused uniform germination of the test plants, unless this was adversely affected by the active compounds.

For the post-emergence treatment, the test plants were first grown to a height of from 3 to 15 cm, depending on the plant habit, and only then treated with the active compounds which had been suspended or emulsified in water. The test plants were for this purpose either sown directly and grown in the same containers, or they were first grown separately as seedlings and transplanted into the test containers a few days prior to treatment. The application rate for the post-emergence treatment was 0.25 or 0.125 kg of a.s. (active substance)/ha.

Depending on the species, the plants were kept at 10–25° C. or 20–35° C. The test period extended over from 2 to 4 weeks. During this time, the plants were tended, and their response to the individual treatments was evaluated.

The evaluation was carried out using a scale from 0 to 100. 100 means no emergence of the plants, or complete destruction of at least the aerial parts and 0 means no damage, or normal course of growth.

The plants used in the greenhouse experiments were of the following species:

| Scientific name | Common name |
| --- | --- |
| Abutilon theophrasti | velvet leaf |
| Avena fatua | wild oat |
| Brachiaria plantaginea | alexandergrass |
| Chenopodium album | lambsquaters |
| Polygonum persicaria | ladysthumb |
| Setaria faberi | giant foxtail |

At application rates of 0.25 or 0.125 kg/ha, the compound 2.1 (Table 2) showed very good post-emergence action against the abovementioned undesirable plants.

We claim:
1. A haloalkyl-substituted 3-(4,5-dihydroisoxazol-3-yl) benzoylcyclohexenone of the formula I

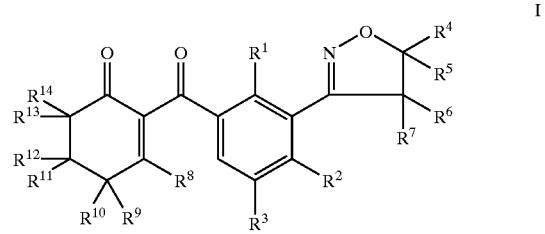

in which
R$^1$ is C$_1$–C$_6$-alkyl, C$_1$–C$_6$-haloalkyl, C$_1$–C$_6$-alkoxy or C$_1$–C$_6$-haloalkoxy;
R$^2$ is C$_1$–C$_6$-alkyl, C$_1$–C$_6$-haloalkyl, C$_1$–C$_6$-alkoxy, C$_1$–C$_6$-haloalkoxy, C$_1$–C$_6$-alkylthio, C$_1$–C$_6$-haloalkylthio, C$_1$–C$_6$-alkylsulfinyl, C$_1$–C$_6$-haloalkylsulfinyl, C$_1$–C$_6$-alkylsulfonyl, C$_1$–C$_6$-haloalkylsulfonyl, halogen, cyano or nitro;
R$^3$ is hydrogen, C$_1$–C$_6$-alkyl or halogen;
R$^4$ is C$_1$–C$_4$-haloalkyl;
R$^5$, R$^6$, R$^7$ independently of one another are hydrogen, C$_1$–C$_4$-alkyl or C$_1$–C$_4$-haloalkyl;
R$^8$ is hydroxyl, mercapto, halogen, OR$^{15}$, SR$^{15}$, SOR$^{16}$ or SO$_2$R$^{16}$;
R$^9$, R$^{13}$ independently of one another are hydrogen, C$_1$–C$_4$-alkyl, C$_1$–C$_4$-alkylthio or C$_1$–C$_4$-alkoxycarbonyl;
R$^{10}$, R$^{12}$, R$^{14}$ independently of one another are hydrogen or C$_1$–C$_4$-alkyl;
R$^{11}$ is hydrogen, hydroxyl, halogen, C$_1$–C$_6$-alkyl, C$_1$–C$_6$-haloalkyl, di(C$_1$–C$_6$-alkoxy)methyl, (C$_1$–C$_6$-alkoxy) (C$_1$–C$_6$-alkylthio)methyl, di(C$_1$–C$_6$-alkylthio)methyl, C$_1$–C$_6$-alkoxy, C$_1$–C$_6$-haloalkoxy, C$_1$–C$_6$-alkylthio, $C_1$–$C_6$-haloalkylthio, $C_1$–$C_6$-alkoxycarbonyl, $C_1$–$C_6$-haloalkoxycarbonyl, 1,3-dioxolan-2-yl, 1,3-dioxan-2-yl, 1,3-oxathiolan-2-yl, 1,3-oxathian-2-yl, 1,3-dithiolan-2-yl or 1,3-dithian-2-yl, where the six lastmentioned radicals may carry one, two or three substituents selected from $C_1$–$C_4$-alkyl; or $R^9$ and $R^{10}$ or $R^{13}$ and $R^{14}$ together are $C_1$–$C_5$-alkanediyl which may carry one, two or three substituents selected from the group consisting of halogen, cyano, $C_1$–$C_4$-alkyl, $C_1$–$C_4$-haloalkyl and $C_1$–$C_4$-alkoxycarbonyl; or $R^{10}$ and $R^{11}$ or $R^{11}$ and $R^{14}$ together are a chemical bond or $C_1$–$C_5$-alkanediyl which may carry one, two or three substituents selected from the group consisting of halogen, cyano, $C_1$–$C_4$-alkyl, $C_1$–$C_4$-haloalkyl and $C_1$–$C_4$-alkoxycarbonyl; or $R^{10}$ and $R^{14}$ together are $C_1$–$C_4$-alkanediyl which may carry one, two or three substituents selected from the group consisting of halogen, cyano, $C_1$–$C_4$-alkyl, $C_1$–$C_4$-alkoxycarbonyl; or $R^{11}$ and $R^{12}$ together are —O—$(CH_2)_p$—O—, —O—$(CH_2)_p$—S—, —S—$(CH_2)_p$—S—, —O—$(CH_2)_q$— or —S—$(CH_2)_q$— which may carry one, two or three substituents selected from the group consisting of halogen, cyano, $C_1$–$C_4$-alkyl, $C_1$–$C_4$-haloalkyl and $C_1$–$C_4$-alkoxycarbonyl; or $R^{11}$ and $R^{12}$ together are an oxygen atom;

$R^{15}$ is $C_1$–$C_6$-alkyl, $C_3$–$C_6$-alkenyl, $C_3$–$C_6$-haloalkenyl, $C_3$–$C_6$-alkynyl, $C_3$–$C_6$-cycloalkyl, $C_1$–$C_{20}$-alkylcarbonyl, $C_2$–$C_{20}$-alkenylcarbonyl, $C_2$–$C_6$-alkynylcarbonyl, $C_1$–$C_6$-alkoxycarbonyl, $C_3$–$C_6$-alkenyloxycarbonyl, $C_3$–$C_6$-alkynyloxycarbonyl, $C_1$–$C_6$-alkylthiocarbonyl, $C_1$–$C_6$-alkylaminocarbonyl, $C_3$–$C_6$-alkenylaminocarbonyl, $C_3$–$C_6$-alkynylaminocarbonyl, N,N-di($C_1$–$C_6$-alkyl)aminocarbonyl, N-($C_3$–$C_6$-alkenyl)-N-($C_1$–$C_6$-alkyl)aminocarbonyl, N-($C_3$–$C_6$-alkynyl)-N-($C_1$–$C_6$-alkyl)aminocarbonyl, N-($C_1$–$C_6$-alkoxy)-N-($C_1$–$C_6$-alkyl)aminocarbonyl, N,N-di($C_1$–$C_6$-alkyl)aminothiocarbonyl, $C_1$–$C_6$-alkoxyimino-$C_1$–$C_6$-alkyl, where the alkyl, alkoxy and cycloalkyl radicals mentioned may be partially or fully halogenated and/or may carry one, two or three substituents selected from the group consisting of cyano, $C_1$–$C_4$-alkoxy, $C_1$–$C_4$-alkylthio, di($C_1$–$C_4$-alkyl)amino, $C_1$–$C_4$-alkylcarbonyl, $C_1$–$C_4$-alkoxycarbonyl, $C_1$–$C_4$-alkoxy-$C_1$–$C_4$-alkoxycarbonyl, $C_1$–$C_4$-alkylaminocarbonyl, N,N-di($C_1$–$C_4$-alkyl)aminocarbonyl and $C_3$–$C_6$-cycloalkyl; is phenyl, phenyl-$C_1$–$C_6$-alkyl, phenylcarbonyl-$C_1$–$C_6$-alkyl, phenylcarbonyl, phenoxycarbonyl, phenoxythiocarbonyl, heterocyclyl, heterocyclyl-$C_1$–$C_6$-alkyl, heterocyclylcarbonyl-$C_1$–$C_6$-alkyl, heterocyclylcarbonyl, heterocyclyloxycarbonyl, heterocyclyloxythiocarbonyl, where the phenyl or heterocyclyl radical of the radicals mentioned may be partially or fully halogenated and/or may carry one, two or three substituents selected from the group consisting of nitro, cyano, $C_1$–$C_4$-alkyl, $C_1$–$C_4$-haloalkyl, $C_1$–$C_4$-alkoxy and $C_1$–$C_4$-haloalkoxy;

$R^{16}$ is $C_1$–$C_6$-alkyl, $C_3$–$C_6$-alkenyl, $C_3$–$C_6$-haloalkenyl, $C_3$–$C_6$-alkynyl or $C_3$–$C_6$-cycloalkyl, where the alkyl and cycloalkyl radicals mentioned may be partially or fully halogenated and/or may carry one, two or three substituents selected from the group consisting of cyano, $C_1$–$C_4$-alkoxy, $C_1$–$C_4$-alkylthio, di($C_1$–$C_4$-alkyl)amino, $C_1$–$C_4$-alkylcarbonyl, $C_1$–$C_4$-alkoxycarbonyl, $C_1$–$C_4$-alkoxy-$C_1$–$C_4$-alkoxycarbonyl, $C_1$–$C_4$-alkylaminocarbonyl, N,N-di($C_1$–$C_4$-alkyl)aminocarbonyl and $C_3$–$C_6$-cycloalkyl; is phenyl, phenyl-$C_1$–$C_6$-alkyl, phenylcarbonyl-$C_1$–$C_6$-alkyl, heterocyclyl, heterocyclyl-$C_1$–$C_6$-alkyl or heterocyclylcarbonyl-$C_1$–$C_6$-alkyl, where the phenyl or heterocyclyl radical of the radicals mentioned may be partially or fully halogenated and/or may carry one, two or three substituents selected from the group consisting of nitro, cyano, $C_1$–$C_4$-alkyl, $C_1$–$C_4$-haloalkyl, $C_1$–$C_4$-alkoxy and $C_1$–$C_4$-haloalkoxy;

p is 2, 3 or 4;

q is 1, 2, 3, 4 or 5;

and its agriculturally useful salts.

2. A haloalkyl-substituted 3-(4,5-dihydroisoxazol-3-yl)benzoylcyclohexenone as claimed in claim 1 in which $R^4$ is fluoromethyl, chloromethyl, bromomethyl, trifluoromethyl, 1-chloro-1-ethyl, 1-fluoro-1-ethyl or pentafluoroethyl.

3. A haloalkyl-substituted 3-(4,5-dihydroisoxazol-3-yl)benzoylcyclohexenone as claimed in claim 1 in which $R^1$ is $C_1$–$C_4$-alkyl;

$R^2$ is $C_1$–$C_6$-haloalkyl, $C_1$–$C_6$-alkylsulfonyl, halogen or nitro; and $R^3$ is hydrogen.

4. A haloalkyl-substituted 3-(4,5-dihydroisoxazol-3-yl)benzoylcyclohexenone as claimed in claim 1 in which $R^9$ and $R^{13}$ independently of one another are hydrogen, $C_1$–$C_4$-alkyl or $C_1$–$C_4$-alkylthio;

$R^{10}$, $R^{12}$, $R^{14}$ independently of one another are hydrogen or methyl and $R^{11}$ is hydrogen, hydroxyl $C_1$–$C_6$-alkyl or di($C_1$–$C_6$-alkoxy)methyl; or $R^9$ and $R^{10}$ or $R^{10}$ and $R^{11}$ or $R^{11}$ and $R^{14}$ or $R^{10}$ and $R^{14}$ or $R^{13}$ and $R^{14}$ together are $C_1$–$C_5$-alkanediyl which may carry one, two or three substituents selected from the group consisting of halogen, cyano, $C_1$–$C_4$-alkyl, $C_1$–$C_4$-haloalkyl and $C_1$–$C_4$-alkoxycarbonyl; or $R^{11}$ and $R^{12}$ together are an oxygen atom.

5. A haloalkyl-substituted 3-(4,5-dihydroisoxazol-3-yl)benzoylcyclohexenone as claimed in claim 1, in which $R^8$ is hydroxyl, $OR^{15}$ or $SR^{15}$; and $R^{15}$ is $C_1$–$C_6$-alkyl, $C_1$–$C_{20}$-alkylcarbonyl, $C_1$–$C_6$-alkoxycarbonyl, $C_1$–$C_6$-alkylthiocarbonyl, where the alkyl and alkoxy radicals may be partially or fully halogenated and/or may carry one, two or three substituents selected from the group consisting of cyano, $C_1$–$C_4$-alkoxy, $C_1$–$C_4$-alkylthio, $C_1$–$C_4$-alkylcarbonyl, $C_1$–$C_4$-alkoxycarbonyl and $C_3$–$C_6$-cycloalkyl; is phenyl, phenyl-$C_1$–$C_4$-alkyl, phenylcarbonyl-$C_1$–$C_4$-alkyl, phenylcarbonyl, phenoxycarbonyl, heterocyclyl, heterocyclyl-$C_1$–$C_4$-alkyl, heterocyclylcarbonyl-$C_1$–$C_4$-alkyl, heterocyclyloxycarbonyl, where the phenyl or heterocyclyl radical of the radicals mentioned may be partially or fully halogenated and/or may carry one, two or three substituents from the group consisting of nitro, cyano, $C_1$–$C_4$-alkyl, $C_1$–$C_4$-haloalkyl, $C_1$–$C_4$-alkoxy and $C_1$–$C_4$-haloalkoxy.

6. A process for preparing haloalkyl-substituted 3-(4,5-dihydroisoxazol-3-yl)benzoylcyclohexenones of the formula I where $R^8$=OH as claimed in claim 1, which comprises acylating a cyclohexenone of the formula II

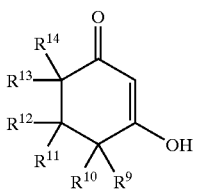

with a benzoic acid derivative III

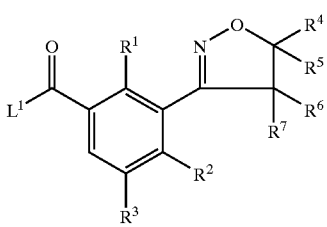

in which $R^1$ to $R^7$ and $R^9$ to $R^{14}$ are as defined in claim 1 and $L^1$ is hydroxyl or a nucleophilically displaceable leaving group and rearranging the acylation product to a compound of the formula I in which $R^8$ is hydroxyl.

7. A process for preparing compounds of the formula I where $R^8=OR^{15}$ or $SR^{15}$ as claimed in claim 1, which comprises reacting a compound of the formula I where R=OH or SH,

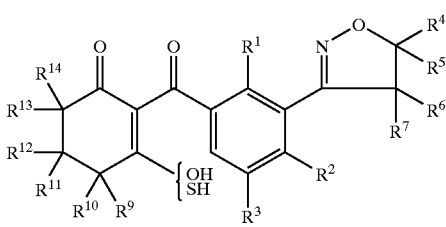

where $R^8$ = OH, SH in which $R^1$ to $R^7$ and $R^9$ to $R^{14}$ are as defined in claim 1 with a compound of the formula VIII $$L^4-R^{15} \qquad \text{VIII}$$

in which the variable $R^{15}$ is as defined in claim 1 and $L^4$ is a nucleophilically displaceable leaving group.

8. A process for preparing compounds of the formula I where $R^8$=halogen as claimed in claim 1, which comprises reacting a compound of the formula I where $R^8$=OH,

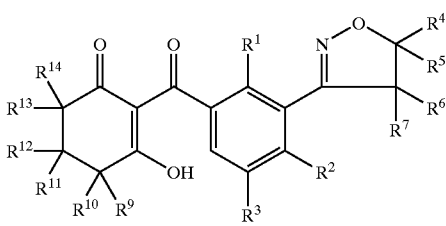

where $R^8$ = OH in which the variables $R^1$ to $R^7$ and $R^9$ to $R^{14}$ are as defined in claim 1 with a halogenating agent.

9. A process for preparing compounds of the formula I where $R^8$=mercapto, $OR^{15}$ or $SR^{15}$ as claimed in claim 1, which comprises reacting a compound of the formula I where $R^8$=halogen,

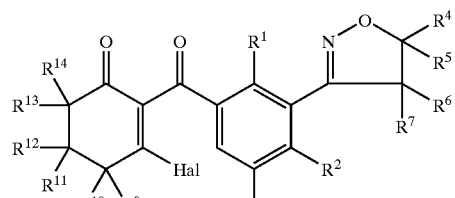

I where $R^8$ = Hal in which the variables $R^1$ to $R^7$ and $R^9$ to $R^{14}$ are as defined in claim 1 with a compound of the formula IX $$H_2S \text{ or } HOR^{15} \text{ or } HSR^{15} \qquad \text{IX}$$

in which $R^{15}$ is as defined in claim 1, if appropriate in the presence of a base.

10. A process for preparing compounds of the formula I where $R^8=SOR^{16}$ or $SO_2R^{16}$ as claimed in claim 1, which comprises reacting a compound of the formula I where $R^8=SR^{16}$,

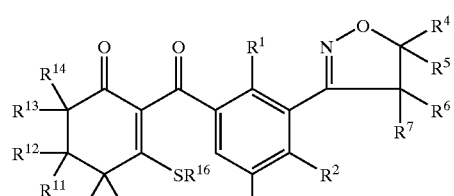

I where $R^8$ = $SR^{16}$ in which the variables $R^1$ to $R^7$ and $R^9$ to $R^{14}$ are as defined in claim 1 with an oxidizing agent.

11. A composition, comprising a herbicidally effective amount of at least one haloalkyl-substituted 3-(4,5-dihydroisoxazol-3-yl)benzoylcyclohexenone of the formula I or an agriculturally useful salt thereof as claimed in claim 1 and auxiliaries customarily used for formulating crop protection agents.

12. A method for controlling undesirable vegetation, which comprises allowing a herbicidally effective amount of at least one haloalkyl-substituted 3-(4,5-dihydroisoxazol-3-yl)benzoylcyclohexenone of the formula I or an agriculturally useful salt thereof as claimed in claim 1, to act on plants, their habitat and/or on seeds.

* * * * *

UNITED STATES PATENT AND TRADEMARK OFFICE
CERTIFICATE OF CORRECTION

PATENT NO. : 6,599,860 B1
DATED : July 29, 2003
INVENTOR(S) : Kudis et al.

It is certified that error appears in the above-identified patent and that said Letters Patent is hereby corrected as shown below:

<u>Column 37,</u>
Line 30, "R=OH" should be -- $R^8$=OH --.

Signed and Sealed this

Tenth Day of February, 2004

JON W. DUDAS
*Acting Director of the United States Patent and Trademark Office*